United States Patent
Fujiyama et al.

(10) Patent No.: US 10,126,234 B2
(45) Date of Patent: Nov. 13, 2018

(54) WATER CONTENT OF A PART OF PLANT EVALUATION METHOD AND WATER CONTENT OF A PART OF PLANT EVALUATION APPARATUS

(71) Applicant: PANASONIC INTELLECTUAL PROPERTY MANAGEMENT CO., LTD., Osaka (JP)

(72) Inventors: Takeshi Fujiyama, Fukuoka (JP); Yuuji Terashima, Fukuoka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 68 days.

(21) Appl. No.: 15/295,065

(22) Filed: Oct. 17, 2016

(65) Prior Publication Data

US 2017/0115210 A1     Apr. 27, 2017

(30) Foreign Application Priority Data

Oct. 23, 2015 (JP) ................. 2015-209230
Oct. 23, 2015 (JP) ................. 2015-209231

(51) Int. Cl.
  *G01N 21/84* (2006.01)
  *G01N 21/3554* (2014.01)
  (Continued)

(52) U.S. Cl.
  CPC ..... *G01N 21/3554* (2013.01); *G01N 21/3151* (2013.01); *G01N 21/359* (2013.01);
  (Continued)

(58) Field of Classification Search
  None
  See application file for complete search history.

(56) References Cited

U.S. PATENT DOCUMENTS 5,001,346 A * 3/1991 Barkhoudarian ....... G01M 3/38
                                                                     250/330
9,128,049 B2 * 9/2015 Groz .................. G01N 21/3151
                                (Continued)

FOREIGN PATENT DOCUMENTS

JP        62-215326         9/1987
JP        03-221843         9/1991
                      (Continued)

OTHER PUBLICATIONS

R.N. Sahoo et al. "Hyperspectral remote sensing of agriculture" Current Science, vol. 108, No. 5, Mar. 10, 2015.*
(Continued)

*Primary Examiner* — Edwin Gunberg
(74) *Attorney, Agent, or Firm* — Greenblum & Bernstein, P.L.C.

(57) ABSTRACT

In a water content evaluation method, when water content of a part of a plant is evaluated, a white reference substrate (background material) is disposed so as to cover a back surface of a leaf of plant. A first beam source radiates a near infrared beam (reference beam) with a wavelength of 905 nm that has a characteristic of tending not to be absorbed in water toward leaf. A second beam source radiates a near infrared beam (measuring beam) with a wavelength of 1550 nm that has a characteristic of tending to be absorbed in water toward the leaf. Threshold level setter/water content index detector calculates a water content index of one leaf that is total sum $\Sigma$ Ln (I905/I1550) of the reflection intensity rate at all irradiation positions of the leaf based on a reflection light of a reference beam and a reflection light of a measuring beam that are reflected on all irradiation positions of the leaf.

19 Claims, 28 Drawing Sheets

(51) Int. Cl.
    *G01N 21/359*     (2014.01)
    *G01N 21/31*     (2006.01)
    *G01N 21/47*     (2006.01)

(52) U.S. Cl.
    CPC ......... *G01N 21/84* (2013.01); *G01N 21/4738* (2013.01); *G01N 2021/3155* (2013.01); *G01N 2021/8466* (2013.01)

(56) References Cited

U.S. PATENT DOCUMENTS

| | | |
|---|---|---|
| 2014/0343863 A1 | 11/2014 | Imanishi et al. |
| 2015/0181137 A1 | 6/2015 | Terashima et al. |
| 2015/0189840 A1 | 7/2015 | Tanizawa et al. |
| 2016/0183488 A1 | 6/2016 | Yano et al. |
| 2016/0198652 A1 | 7/2016 | Yano et al. |

FOREIGN PATENT DOCUMENTS

| | | |
|---|---|---|
| JP | 10-090066 | 4/1998 |
| JP | 2001-272373 | 10/2001 |
| JP | 05258044 | 8/2013 |
| JP | 2014-240831 | 12/2014 |

OTHER PUBLICATIONS

Motoko Fujino et al., "Nondestructive Instrumentation of Water-stressed Cucumber Leaves", The University of Tokyo, Graduate School of Agricultural and Life Sciences, Agricultural Information Research 11(2), pp. 161-170 (2002), together with an English language translation.

International Search Report and Written Opinion of PCT Application No. PCT/JP2016/004610 dated Jan. 11, 2017.

\* cited by examiner

FIG. 10

| REFLECTION INTENSITY RATE Ln (I905/I1550) | INTENSITY RATIO (I905/I1550) |
|---|---|
| <0.3 | <1.349 |
| 0.3~0.4 | 1.349~1.492 |
| 0.4~0.5 | 1.492~1.649 |
| 0.5~0.55 | 1.649~1.733 |
| 0.55~0.6 | 1.733~1.822 |
| 0.6~0.75 | 1.822~2.117 |
| 0.75< | 2.117< |

| 0.120811 | 0.149614 | 0.137343 | 0.114148 | 0.076093 | 0.011674 | -0.01163 | -0.05523 | -0.03757 |
| --- | --- | --- | --- | --- | --- | --- | --- | --- |
| 0.125248 | 0.172965 | 0.15948 | 0.126022 | 0.089612 | 0.01949 | 0.011873 | -0.03391 | -0.01574 |
| 0.148199 | 0.199904 | 0.17691 | 0.133531 | 0.111832 | 0.044927 | 0.052822 | 0.008977 | 0.022246 |
| 0.194251 | 0.227869 | 0.198172 | 0.156277 | 0.154876 | 0.102169 | 0.119502 | 0.074724 | 0.075352 |
| 0.247982 | 0.262199 | 0.239978 | 0.215673 | 0.229191 | 0.192649 | 0.214218 | 0.156125 | 0.136483 |
| 0.276739 | 0.287792 | 0.295587 | 0.296691 | 0.326487 | 0.302588 | 0.32026 | 0.237615 | 0.191142 |
| 0.254583 | 0.278097 | 0.324702 | 0.364308 | 0.412217 | 0.409069 | 0.410649 | 0.302116 | 0.230093 |
| 0.199545 | 0.234741 | 0.302685 | 0.394193 | 0.454575 | 0.470076 | 0.45354 | 0.329293 | 0.250862 |
| 0.15815 | 0.197794 | 0.272265 | 0.394631 | 0.455677 | 0.485935 | 0.461736 | 0.330715 | 0.251775 |
| 0.161212 | 0.206592 | 0.282619 | 0.409233 | 0.458335 | 0.474655 | 0.45055 | 0.321021 | 0.242244 |
| 0.204409 | 0.269788 | 0.342894 | 0.450824 | 0.474401 | 0.460903 | 0.427522 | 0.301546 | 0.219295 |
| 0.256744 | 0.348575 | 0.412386 | 0.497288 | 0.490421 | 0.435941 | 0.390092 | 0.270651 | 0.186504 |
| 0.292105 | 0.406767 | 0.453507 | 0.506656 | 0.485508 | 0.402278 | 0.333838 | 0.226336 | 0.146093 |
| 0.295668 | 0.42312 | 0.463995 | 0.481857 | 0.449536 | 0.350517 | 0.26229 | 0.180838 | 0.103744 |
| 0.265075 | 0.398231 | 0.445507 | 0.423915 | 0.374375 | 0.281667 | 0.181745 | 0.129034 | 0.062051 |
| 0.214678 | 0.344539 | 0.393603 | 0.348569 | 0.277132 | 0.203423 | 0.103611 | 0.077881 | 0.01823 |
| 0.169447 | 0.275706 | 0.315009 | 0.261335 | 0.175947 | 0.124205 | 0.031069 | 0.018942 | -0.01898 |
| 0.141768 | 0.214221 | 0.230803 | 0.178572 | 0.093177 | 0.062106 | -0.02083 | -0.01928 | -0.02509 |
| 0.1265 | 0.162033 | 0.159463 | 0.116279 | 0.041841 | 0.020169 | -0.03136 | -0.01489 | 0.004509 |
| 0.094079 | 0.112334 | 0.093124 | 0.074864 | 0.023198 | 0.023857 | -0.00217 | 0.025928 | 0.059011 |
| 0.043646 | 0.055988 | 0.032287 | 0.048581 | 0.024701 | 0.045375 | 0.056402 | 0.089247 | 0.11396 |

ARE

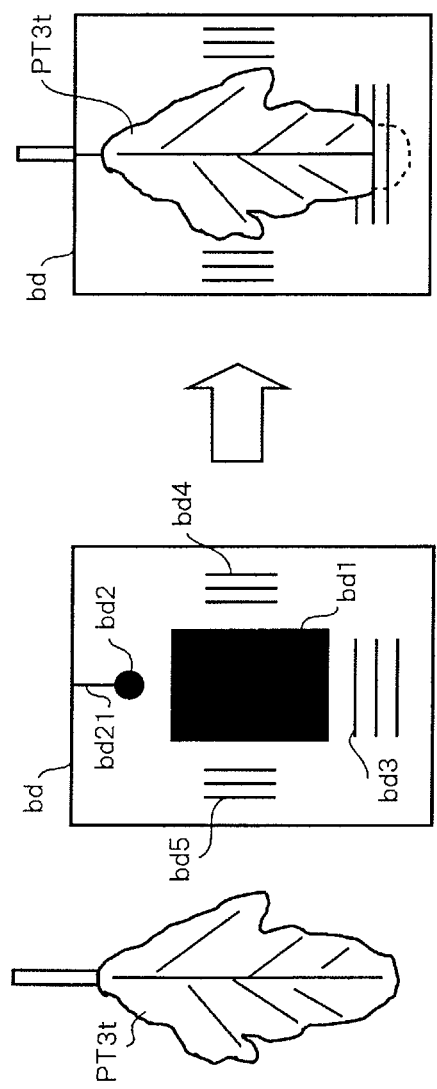

WATER CONTENT OF A PART OF PLANT EVALUATION METHOD AND WATER CONTENT OF A PART OF PLANT EVALUATION APPARATUS

BACKGROUND

1. Field of the Invention

The present disclosure relates to a water content evaluation method and a water content evaluation apparatus which measures water content contained in a leaf or a part of plant.

2. Description of the Related Art

There is a potential difference inside and outside of a cell in a normal plant and electromotive force is generated. It is possible to describe a mechanism which generates such electromotive force based on, for example, an electrophysiological model of an axial organ of a higher plant. In particular, various methods are suggested in which a state of a root of the plant (for example, water stress) is examined non-destructively utilizing electromotive force between the root and soil.

As a technique in which water stress in a plant is measured utilizing the method described above, for example, JP-A-2001-272373 discloses connecting a first nonpolarizable electrode to the plant, connecting a second nonpolarizable electrode to soil in which the plant is planted, providing a potentiometer between the two nonpolarizable electrodes, and being able to measure water stress which is received by the plant by measuring electromotive force between both nonpolarizable electrodes using the potentiometer.

In a case where water content that is contained in a leaf is measured by irradiating the leaf of the plant with a near infrared beam and status of the plant is evaluated, the configuration in PTL 1 has the following problem. The leaf of the plant performs movement such as contraction by bending or coiling, and opening or closing in the morning, in the afternoon, and in the evening, daily or in increments of time.

In a case where water content is measured which is contained in the leaf by irradiating the leaf of the plant with the near infrared beam and status of the plant is evaluated, the leaf of the plant performs movement such as contraction by bending or coiling, and opening or closing in the morning, in the afternoon, and in the evening, daily or in increments of time. Thickness of the leaf changes in an optical axis direction according to the movement of the leaf. For example, when angle θ is inclined to the front due to the leaf that stands in a vertical direction with respect to the optical axis bending, the thickness of the leaf in the optical axis direction is raised by (1/cos θ). The increase in the thickness is obtained by a measurement result in which the water content that is contained in the leaf is greater than in reality. In addition, when measuring by irradiating a front surface of the leaf with the near infrared beam at a predetermined spot diameter, the leaf is damaged from a portion of an irradiation range due to movement of the leaf, an irradiation area (projection area) of the leaf is small, and the measurement result is obtained in which the water content is lower than in reality.

In this manner, an error may be generated in measurement precision of the water content of the leaf, and it may not be possible to correctly evaluate status of the plant since accurate water content is not obtained.

In addition, the leaves of a seedling in a field grow in abundance and are foliage. In the foliage, a plurality of leaves overlap is respective orientations, and for example, when wind blows, the leaves relatively move.

Since the water content which is contained in the leaf is measured by irradiating the leaf of the plant with the near infrared beam and status of the plant is evaluated, in a case where the front surface of the leaf of the plant is irradiated with two types of near infrared beams and water content is obtained from a reflection intensity rate therefrom, the radiated near infrared beam is absorbed and scattered due to the leaf on a periphery of a leaf that is a measurement target (refer to FIG. 21A). Other than, for example, the radiated near infrared beam being absorbed by the leaf that is the measurement target, a leaf on the left side is also radiated and a portion is absorbed. The leaf on the left side is radiated, and the near infrared beam that is scattered by the leaf on the left side is diffused on the leaf that is the measurement target. In addition, multiple scattering also occurs in which a leaf on the right side is radiated, and diffused light that is scattered by the leaf on the right side is diffused to another leaf and is diffused on the leaf that is the measurement target. Since the background of the reflection intensity rate that is obtained by measurement is significantly raised, the multiple scattering is difficult to distinguish individually to the leaf that is the measurement target and the leaves on the periphery of the measurement target. In addition, the plurality of leaves overlap or are separated, and a target area of the leaf on which the near infrared beam is radiated changes (refer to FIG. 21B).

Accordingly, even in measurement of presence or absence of water content, individual leaves on the periphery and the target leaf are difficult to distinguish.

SUMMARY

The present disclosure has an object of accurately measuring water content which is contained in a measurement target such as a leaf or a part of plant.

Furthermore, the present disclosure has an object of eliminating influence due to scattered light (light scattered externally) from a peripheral leaf and accurately measuring water content of the leaf or the part of plant that is the measurement target even within foliage in which multiple leaves grow in abundance.

According to an aspect of the present disclosure, there is provided a water content evaluation apparatus including a first light source which radiates a near infrared laser reference beam of a first wavelength that has a characteristic in which light tends not to be absorbed in water while sequentially scanning toward a plant, a second light source which radiates a near infrared laser measuring beam of a second wavelength that has a characteristic in which light tends to be absorbed in water while sequentially scanning toward the plant, and a water content calculation unit which calculates water content at all irradiation positions of the plant based on a reflection light of the near infrared laser reference beam that is reflected on all irradiation positions of the plant and a reflection light of the near infrared laser measuring beam that is reflected on all irradiation positions of the plant.

According to another aspect of the present disclosure, there is provided a water content evaluation apparatus including a first light source which radiates a near infrared laser reference beam of a first wavelength that has a characteristic in which light tends not to be absorbed in water while sequentially scanning toward an irradiation area which includes a background material that covers a back surface of a part of the water content evaluation apparatus that is set as an evaluation target and a part of the plant that is set as an evaluation target, a second light source which radiates a near infrared laser measuring beam of a second wavelength that has a characteristic in which light tends to be absorbed in water while sequentially scanning toward the irradiation area, an identification unit which identifies the part of the irradiation area that is the evaluation target based on a reflection light of the near infrared laser reference beam that is reflected on the irradiation area and a reflection light of the near infrared laser measuring beam that is reflected on the irradiation area, and a water content calculation unit which calculates water content in the part that is the evaluation target which is identified by the identification unit.

According to still another aspect of the present disclosure, there is provided a water content evaluation method in the water content evaluation apparatus, the method including: causing a first light source to radiate a near infrared laser reference beam of a first wavelength that has a characteristic in which light tends not to be absorbed in water while sequentially scanning toward a plant; causing a second light source to radiate a near infrared laser measuring beam of a second wavelength that has a characteristic in which light tends to be absorbed in water while sequentially scanning toward the plant; and calculating water content at all irradiation positions of the plant based on a reflection light of the near infrared laser reference beam that is reflected on all irradiation positions of the plant and a reflection light of the near infrared laser measuring beam that is reflected on all irradiation positions of the part of the plant.

According to still another aspect of the present disclosure, there is provided a water content evaluation method in the water content evaluation apparatus which evaluates water content of a part of a plant, the method including: disposing a background material which covers a back surface of a part of the plant that is set as an evaluation target of the water content evaluation apparatus; causing a first light source to radiate a near infrared laser reference beam of a first wavelength that has a characteristic in which light tends not to be absorbed in water while sequentially scanning toward an irradiation area which includes the part that is set as the evaluation target and a background material; causing a second light source to radiate a near infrared laser measuring beam of a second wavelength that has a characteristic in which light tends to be absorbed in water while sequentially scanning toward the irradiation area, and identifying the part of the irradiation area that is set as the evaluation target based on a reflection light of the near infrared laser reference beam that is reflected on the irradiation area and a reflection light of the near infrared laser measuring beam that is reflected on the irradiation area to calculate water content in the part that is the evaluation target.

According to the aspects of the present disclosure, it is possible to accurately measure water content which is contained in the measurement target.

Furthermore, according to the aspects of the present disclosure, in a case where the measurement target is, for example, a leaf or a part of plant, it is possible to eliminate influence due to scattered light (light scattered externally) from the peripheral leaf and accurately measure the water content of the leaf or the part of the plant that is the measurement target even within the foliage in which multiple leaves grow in abundance.

BRIEF DESCRIPTION OF THE DRAWINGS

FIG. 10 is a table illustrating a tone color corresponding to the reflection intensity rate;

FIG. 11 is a table illustrating the reflection intensity rate in a portion of a frame image which includes a pixel space that the leaf occupies;

FIG. 23 is a diagram which describes attachment of the leaf on the white reference substrate;

FIG. 26A is a table illustrating the reflection intensity rate in a portion of a frame image which includes a pixel space that the leaf occupies which is covered by the back surface on the white reference substrate;

FIG. 26B is a table illustrating the reflection intensity rate in a portion of the frame image which includes the pixel space that the leaf occupies which is not covered by the back surface on the white reference substrate;

DETAILED DESCRIPTION

Details and Problems of First Embodiment

As a method for obtaining water content of a leaf or a part of a plant remotely without breaking the leaf, the present inventor and the like suggests a method of irradiating the front surface of the leaf with two types of near infrared beams and obtaining water from the reflection intensity rate. One near infrared beam out of the two types of near infrared beams is a laser beam which has, for example, a wavelength of 905 nm, and is used as a reference beam which is transmitted through water. The other near infrared beam is the laser beam which has, for example, a wavelength of 1550 nm, and is used as a measuring beam which is absorbed in water. The reference beam and the measuring beam are radiated two times on the front surface of the leaf, and the reflection light is received by an invisible light camera. Light is received by the invisible light camera, and reflection intensity rate Ln (I905/I1550) which is a reflection intensity rate of the reference beam and reflection intensity of the measuring beam is a value which is equivalent to water content at an irradiation position.

Figure 7A:
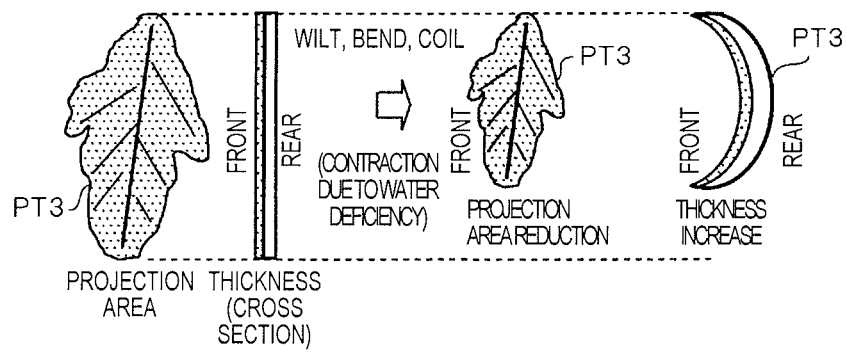
FIG. 7A is a diagram which describes a summary of an operation which measures a reflection intensity rate of the entirety of a leaf.
Figure 7B:
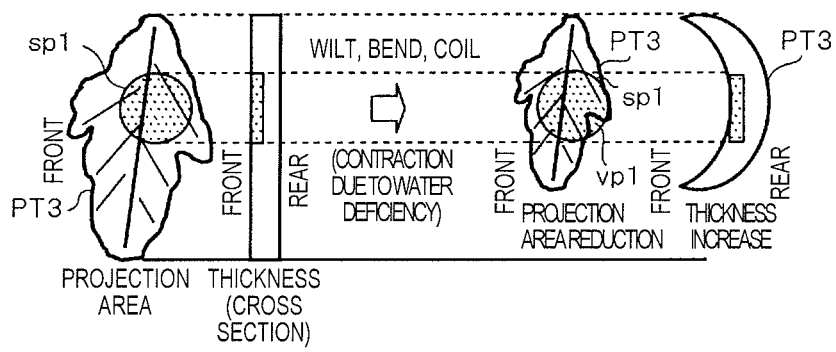
FIG. 7B is a diagram which describes a summary of an operation that measures the reflection intensity rate in which a spot is in a fixed area.

As shown in FIG. 7B, a laser beam is radiated within a range of a spot diameter (for example, 20 mmφ) smaller than the front surface of leaf PT3 while sequentially scanning, and an average surface reflection intensity rate is obtained in spot sp1. Water content per unit area is presumed from the average surface reflection intensity rate. However, it is already known that correlation between water content per unit area and water potential is low (refer to as follows: "Nondestructive Instrumentation of Water-stressed Cucumber Leaves" Comparison between Changes in Spectral Reflectance, Stomatal Conductance, PSII Yield and Shape The University of Tokyo, Graduate School of Agricultural and Life Sciences, Agricultural Information Research, Vol. 11 (2002), No. 2, p. 161-170). Water potential is a value which represents water retention capability (water content) of the plant, and is an index which measures status (in other words, degree of health) of the plant.

The shape of the leaf is not fixed to a key factor of the correlation between water content per unit area and water potential being low, and is considered to change according to wilting, bending, coiling, and the like. The leaf of the plant performs movement by bending or coiling and opening or closing (contracting) in the morning, in the afternoon, and in the evening, daily or in increments of time.

In a case where water content is measured by radiating the near infrared beam, thickness of the leaf changes in an optical axis direction according to the movement of the leaf. For example, when angle θ is inclined to the front due to leaf PT3 that stands in a vertical direction with respect to the optical axis bending, the thickness of the leaf in the optical axis direction is raised by (1/cos θ). The increase in the thickness is obtained by a measurement result in which the water content that is contained in leaf PT3 is greater than in reality. In addition, when measuring by irradiating a front surface of the leaf with the near infrared beam at a predetermined spot diameter, leaf PT3 is damaged from portion vp1 of an irradiation range due to movement of the leaf, an irradiation area (projection area) of the leaf is small, and the measurement result is obtained in which the water content is lower than in reality.

Accordingly, even if the near infrared beam (laser beam) is radiated in the spot, and the water content per unit time of the leaf is measured, status of the leaf cannot be understood well.

Therefore, in the first embodiment, it is possible to accurately measure water content which is contained in the plant that is the index of status of the plant.

First Embodiment

A first embodiment, which specifically exemplifies the water content evaluation apparatus and the water content evaluation method according to the present disclosure, will be described in detail with reference to the accompanying drawings. However, detailed description may be omitted as necessary. For example, detailed description of already well-known matter and overlapping description with respect to substantially the same configuration may be omitted. This is because the following description is prevented from unnecessarily becoming redundant, and a process of the inventor is easily set. Note that, drawings and the following description are provided by the inventor for sufficient understanding of the present disclosure, and thereby, the present disclosure is not intended to be limited to a subject described in the range of the claims.

Figure 1:
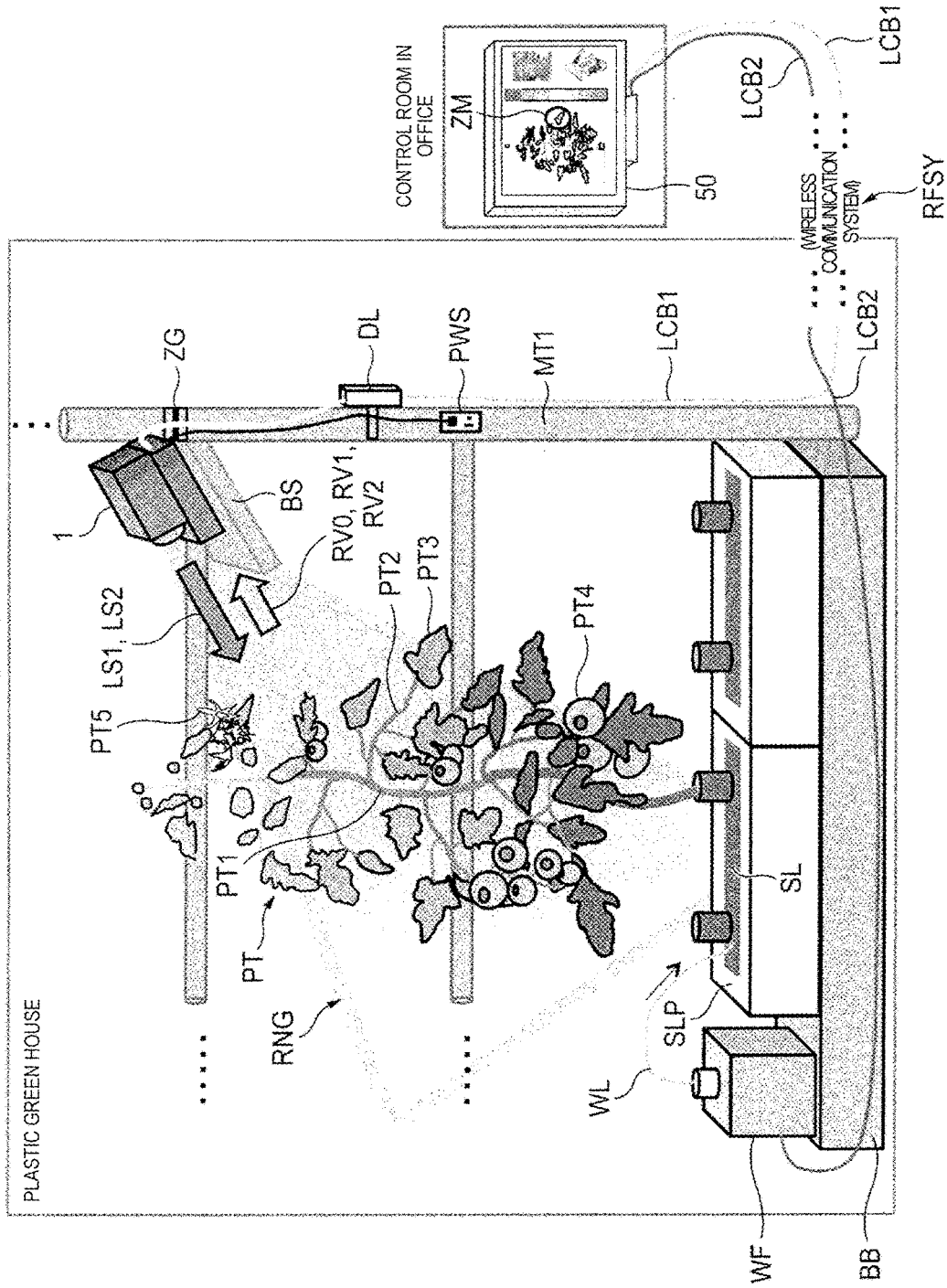
FIG. 1 is a conceptual explanatory diagram illustrating an example of usage circumstances of a detection camera in a first embodiment.

Description is made exemplifying detection camera 1 indicated in FIG. 1 as an example of the water content evaluation apparatus of the present embodiment. The present embodiment is able to be expressed as the water content evaluation method which executes each process that is performed by the detection camera. Detection camera 1 of the present embodiment is able to detect a distribution state of presence or absence of water content of the leaf or the part of the plant.

Here, an observation target of detection camera 1 of the present embodiment is the leaf or the part of the plant, and description is made by exemplifying a fruit vegetable that is given as a more specific example. Since sugar content of a fruit of a tomato is increased in growth of fruit vegetables such as, for example, the tomato, it is known that it is necessary for water or fertilizer to be in an insufficient state and not a state in which water or fertilizer is sufficiently supplied as a result of water or fertilizer of a root or a leaf being digested by a suitable amount in photosynthesis. For example, if sufficient water is supplied to the leaf, the leaf has a flat shape in a sound state. Meanwhile, when water of the leaf is equivalently insufficient, the shape of the leaf is bent. Meanwhile, when fertilizer in the soil is equivalently insufficient, a condition is generated of the leaf turning yellow and the like.

In the present embodiment below, an example is described in which detection camera 1 radiates laser beams of a plurality of types which are different in wavelength on the plant (for example leaf), and detects water content of the leaf based on an intensity rate of respective diffuse reflection light that are reflected on irradiation positions of the leaf. Note that, in the present embodiment, the leaf of the plant is the measurement target, but the measurement target is not limited to the leaf, and may be other parts of a seed, stalk, flower, and the like. A second embodiment is also the same.

Outline of Detection Camera

FIG. 1 is a conceptual explanatory diagram illustrating an example of usage circumstances of detection camera 1 in the first embodiment. Detection camera 1 is installed at a fixed point within a plastic greenhouse in which, for example, fruit vegetables such as the tomato are planted. In detail, for example, detection camera 1 is installed on base BS that is fixed to mounting jig ZG which is attached so as to interpose support column MT1 with a cylindrical shape extend in a vertical direction from the ground. Detection camera 1 operates by a power source to be supplied from power source switch PWS that is attached to support column MT1, and radiates reference beam LS1 and measuring beam LS2 that are a plurality of types of laser beams which have different wavelengths toward plant PT that is the observation target across irradiation range RNG.

Plant PT is, for example, a fruit vegetable plant such as the tomato, a root of plant PT which grows from soil SL that is filled in soil pot SLP which is installed on base BB, and plant PT has each of stem PT1, stalk PT2, leaf PT3, fruit PT4, and flower PT5. Fertilizer water supply device WF is installed on base BB. Fertilizer water supply device WF supplies water to soil spot SLP via, for example, cable WL according to an instruction from wireless communication system RFSY that is connected via local area network (LAN) cable LCB2. Thereby, since water is supplied to soil SL, the root of plant PT absorbs water, and transmits water to each part within plant PT (that is, stem PT1, stalk PT2, leaf PT3, fruit PT4, and flower PT5).

In addition, detection camera 1 receives diffuse reflection light RV1 and RV2 that are reflected on an irradiation position of plant PT which is radiated by reference beam LS1 and measuring beam LS2, and furthermore, receives ambient light RV0. As will be described later, detection camera 1 has a normal camera function, and is able to image an image (that is, image of plant PT within the plastic greenhouse indicated in FIG. 1) within a default angle of view due to ambient light RV0 entering. Detection camera 1 outputs output data which includes various detection results (refer to description below) or image data to data logger DL based on diffuse reflection light RV1 and RV2.

Data logger DL transmits output data from detection camera 1 to management personal computer (PC) of a control room within an office at a position geographically separated from the plastic greenhouse via LAN cable LCB1 and wireless communication system RFSY. Wireless communication system RFSY is not particularly limited in communication specification, but controls communication between data logger DL within the plastic greenhouse and management PC within the control room in the office, and furthermore transmits an instruction from management PC which relates to supply of water or fertilizer of soil spot SLP to fertilizer water supply device WF.

Monitor 50 is connected to management PC within the control room in the office, and management PC displays output data of detection camera 1 that is transmitted from data logger DL on monitor 50. In FIG. 1, for example, monitor 50 displays the entirety of plant PT that is the monitoring target and a distribution state which relates to presence or absence of water in the entirety of plant PT. In addition, monitor 50 generates and is able to comparatively display an enlargement distribution state of a specific designated location out of the entirety of plant PT (that is, designated location ZM that is specified by a zoom operation of an observer who uses management PC) and image data corresponding to the designated location of the enlargement distribution state.

Detection camera 1 has a configuration which includes visible light camera VSC and invisible light sensor NVSS. Visible light camera VSC (acquiring unit) images plant PT within the plastic greenhouse using ambient light RV0 with respect to invisible light that has a predetermined wavelength (for example, 0.4 to 0.7 μm) in the same manner as, for example, existing monitoring camera. Image data of the plant that is imaged by visible light camera VSC refers to "visible light camera image data".

Invisible light sensor NVSS incidents reference beam LS1 and measuring beam LS2 which is invisible light (for example, infrared beam) that has a plurality of types of wavelengths (refer to description below) with respect to the same plant PT as invisible light sensor VSC. Invisible light sensor NVSS detects presence or absence of water at the irradiation position of plant PT which is the monitoring target using the intensity rate of diffuse reflection light RV1 and RV2 that are reflected on the irradiation position of plant PT which is radiated by reference beam LS1 and measuring beam LS2.

In addition, in visible light camera image data that is imaged by visible light camera VSC, detection camera 1 generates and outputs output image data (hereinafter referred to as "detection result image data") which is equivalent to the detection result of water of invisible light sensor NVSS or display data that composites information which relates to detection result image data. Display data is not limited to image data in which detection result image data and visible light camera image data are composited, and for example, may be image data that is generated such that detection result image data and visible light camera image data are able to be compared. An output destination of the display data from detection camera 1 is an externally connected device that is connected to detection camera 1 via, for example, a network, and is data logger DL or communication terminal MT (refer to FIG. 2). The network may be a wired network (for example, intranet or internet), and may be a wireless network (for example, wireless LAN).

Description of Each Part of Detection Camera

Figure 2:
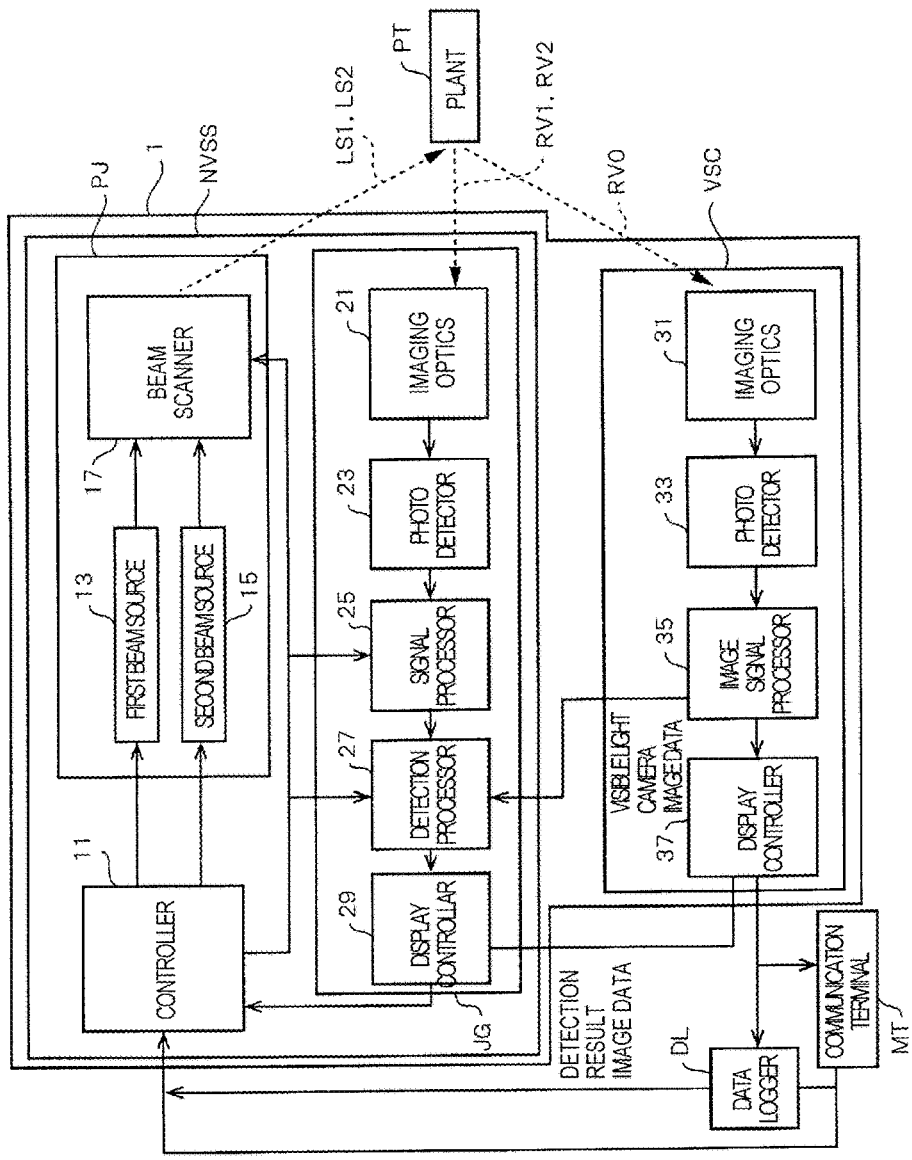
FIG. 2 is a block diagram illustrating in detail an example of an internal configuration of the detection camera.

FIG. 2 is a block diagram illustrating in detail an example of an internal configuration of detection camera 1. Detection camera 1 which is indicated in FIG. 2 has a configuration which includes invisible light sensor NVSS and visible light camera VSC. Invisible light sensor NVSS has a configuration which includes controller 11, beam output PJ, and determiner JG. Beam output PJ has first beam source 13, second beam source 15, and beam scanner 17. Determiner JG has imaging optics 21, photo detector 23, signal processor 25, detection processor 27, and detection processor 29. Visible light camera VSC has imaging optics 31, photo detector 33, image signal processor 35, and display controller 37. Communication terminal MT is portable by a user (for example, observer of growth of plant PT of fruit vegetable plant such as the tomato, hereinafter the same).

In the description of each part of detection camera 1, controller 11, invisible light sensor NVSS, and visible light sensor VSC are described in order.

Controller 11 is configured using, for example, a central processor (CPU), a micro processor (MPU), or a digital signal processor (DSP), (and also configured using, for example, a program memory and a work memory,) and performs a signal process for totally controlling an operation control of each part of visible light sensor VSC and invisible light sensor NVSS, an input and output process of data within other parts, a computing process of data, and a storage process of data. In addition, controller 11 includes timing controller 11a described later (refer to FIG. 3).

Controller 11 sets detection threshold level M of plant PT which is the detection target of invisible light sensor NVSS to detection processor 27 described later. Details of the operation of controller 11 will be described later with reference to FIG. 4.

Timing controller 11a controls output of first beam source 13 and second beam source 15 in beam output PJ. In detail, timing controller 11a outputs timing signal for beam scanning TR to first beam source 13 and second beam source 15 in a case where light is incident to first beam source 13 and second beam source 15.

In addition, during the start of a predetermined incidence period, timing controller 11a alternately outputs beam output signal RF to first beam source 13 and second beam source 15. In detail, during the start of the incidence period of an odd number of times, timing controller 11a outputs beam output signal RF to first beam source 13 and during the start of the incidence period of an even number of times, outputs beam output signal RF to second beam source 15.

Next, each part of invisible light sensor NVSS is described.

When first beam source 13 as an example of the first light source receives timing signal for beam scanning TR from timing controller 11a of controller 11, reference beam LS1 (for example, near infrared beam) that is a laser beam of invisible light that has a predetermined wavelength (for example, 905 nm) is incident on plant PT via beam scanner 17 according to beam output signal RF from timing controller 11a in each incidence period (default value) of an odd number of times.

Note that, presence or absence of detection of water in plant PT may be determined by comparing to the predetermined detection threshold level M. Detection threshold level M may be a predetermined value, may be an arbitrarily set value, and furthermore, may be a value based on intensity of the diffuse reflection light that is acquired in a state in which there is no water (for example, a value in which a predetermined margin is added to a value of intensity of the diffuse reflection light that is obtained in a state in which there is no water). That is, presence or absence of detection of water may be determined by comparing detection result image data that is acquired in a state in which there is no water and detection result image data that is acquired thereafter. In this manner, it is possible to set a threshold level appropriate for an environment in which detection camera 1 is installed as detecting threshold level M of presence or absence of water by acquiring intensity of the diffuse reflection light in the state in which there is no water.

When second beam source 15 as an example of the second light source receives timing signal for beam scanning TR from timing controller 11a of controller 11, measuring beam LS2 (for example, infrared beam) that is the laser beam of invisible light that has a predetermined wavelength (for example, 1550 nm) is incident on plant PT via beam scanner 17 according to beam output signal RF from timing controller 11a in each incidence period (default value) of an even number of times. In the present embodiment, measuring beam LS2 that is incident from second beam source 15 is used in determination of presence or absence of detection of water in plant PT. Wavelength 1550 nm of measuring beam LS2 is a wavelength which has a characteristic in which light tends to be absorbed in water (refer to FIG. 6).

Furthermore, detection camera 1 detects presence or absence of water at the irradiation position of plant PT that is radiated by reference beam LS1 and measuring beam LS2 using diffuse reflection light RV1 of reference beam LS1 as reference data for detecting water at the irradiation position of plant PT, and using diffuse reflection light RV2 at the irradiation position of plant PT that is radiated by measuring beam LS2 and diffuse reflection light RV1 of reference beam LS1. Accordingly, detection camera 1 is able to detect water of plant PT with high precision using reference beam LS1 and measuring beam LS2 of two types of wavelengths that detect water in plant PT differently and diffuse reflection lights RV1 and RV2 thereof.

Beam scanner 17 two-dimensionally scans reference beam LS1 which is incident from first beam source 13 and measuring beam LS2 which is incident from second beam source 15 with respect to plant PT that is present in a detection area in invisible light sensor NVSS. Thereby, detection camera 1 detects presence or absence of water at the irradiation position of plant PT that is radiated by reference beam LS1 and measuring beam LS2 based on diffuse reflection light RV2 that is reflected at the irradiation position of plant PT by measuring beam LS2 and diffuse reflection light RV1 described above.

Figure 3:
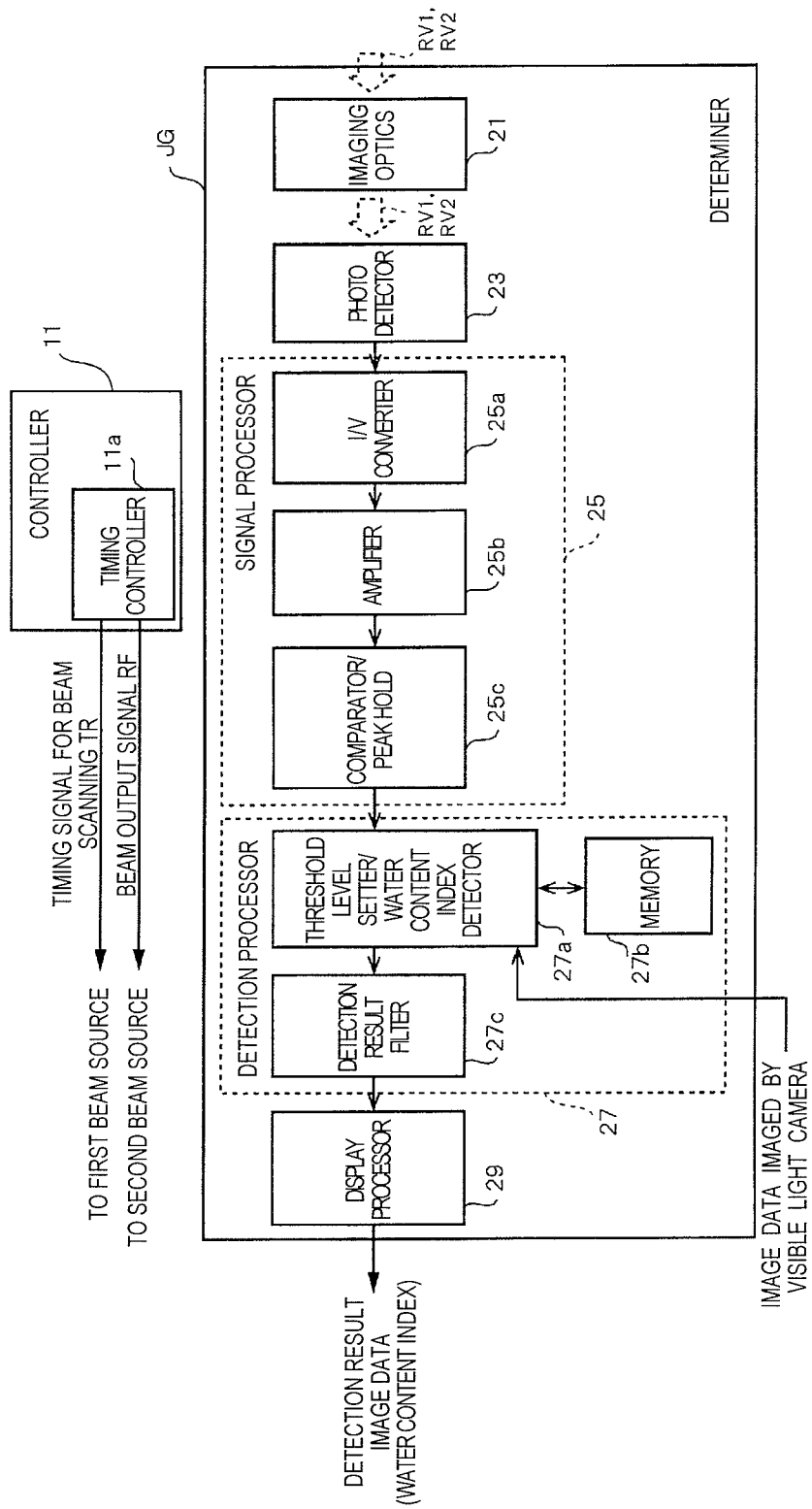
FIG. 3 is a diagram illustrating in detail an example of an internal configuration of a determiner of the detection camera.

Next, an internal configuration of determiner JG is described in detail with reference to FIGS. 2 and 3. FIG. 3 is a diagram illustrating in detail an example of an internal configuration of a determiner JG of detection camera 1.

Imaging optics 21 is configured using, for example, a lens, light (for example, diffuse reflection light RV1 or diffuse reflection light RV2) which is incident from outside of detection camera 1 is concentrated, and diffuse reflection light RV1 or diffuse reflection light RV2 form an image on a predetermined imaging area of photo detector 23.

Photo detector 23 is an image sensor which has a peak of spectral sensitivity with respect to wavelengths of both of reference beam LS1 and measuring beam LS2. Photo detector 23 converts an optical image of diffuse reflection light RV1 or diffuse reflection light RV2 that form an image on the imaging area to an electrical signal. Output of photo detector 23 is input to signal processor 25 as the electrical signal (current signal). Note that, imaging optics 21 and photo detector 23 functions as an imaging unit in invisible light sensor NVSS.

Signal processor 25 has I/V converter 25a, amplifier 25b, and comparator/peak hold 25c. I/V converter 25a converts the current signal that is an output signal (analog signal) of photo detector 23 to a voltage signal. Amplifier 25b amplifies a level of the voltage signal that is the output signal (analog signal) of I/V converter 25a up to a processable level in comparator/peak hold 25c.

Comparator/peak hold 25c binarizes the output signal of amplifier 25b and outputs to threshold level setter/water content index (index of water content) detector 27a according to a comparative result of the output signal (analog signal) of amplifier 25b and the predetermined threshold level. In addition, comparator/peak hold 25c includes an analog digital converter (ADC), detects and holds the peak of an analog digital (AD) converter result of the output signal (analog signal) of amplifier 25b and furthermore, outputs peak information to threshold level setter/water content index detector 27a.

Detection processor 27 has threshold level setter/water content index detector 27a, memory 27b, and detection result filter 27c. Threshold level setter/water content index detector 27a (threshold level holder) generates and registers frequency distribution data in advance (refer to FIG. 14). Frequency distribution data indicates frequency distribution of the reflection intensity rate (water content index) in all pixels or one frame image. As will be described later, threshold level setter/water content index detector 27a (threshold level calculation unit) is set by calculating threshold level Sh of the reflection intensity rate for identifying the shape of the leaf using the frequency distribution data.

In addition, threshold level setter/water content index detector 27a detects presence or absence of water at the irradiation position of reference beam LS1 and measuring beam LS2 of plant PT based on output (peak information) of comparator/peak hold 25c in diffuse reflection light RV1 of reference beam LS1 and output (peak information) of comparator/peak hold 25c in diffuse reflection light RV2 of measuring beam LS2.

In detail, threshold level setter/water content index detector 27a temporarily stores, for example, output (peak information) of comparator/peak hold 25c in diffuse reflection light RV1 of reference beam LS1 in memory 27b, and next, waits until the output (peak information) of comparator/peak hold 25c in diffuse reflection light RV2 of measuring beam LS2 is obtained. Threshold level setter/water content index detector 27a obtains output (peak information) of comparator/peak hold 25c in diffuse reflection light RV2 of measuring beam LS2, and then calculates a ratio of output (peak information) of comparator/peak hold 25c in diffuse reflection light RV1 of reference beam LS1 and output (peak information) of comparator/peak hold 25c in diffuse reflection light RV2 of measuring beam LS2 in the same line of plant PT that are contained in the angle of view with reference to memory 27b.

For example, at the irradiation position at which there is water, since a portion of measuring beam LS2 tends to be absorbed, intensity (that is, amplitude) of diffuse reflection light RV2 is attenuated. Accordingly, it is possible for threshold level setter/water content index detector 27a to detect presence or absence of water at the irradiation position of reference beam LS1 and measuring beam LS2 based on a calculation result (for example, calculation result of difference (difference $\Delta V$ of amplitude) of each intensity of diffuse reflection light RV1 and diffuse reflection light RV2 or intensity ratio of diffuse reflection light RV1 and diffuse reflection light RV2) of each line of plant PT which is contained in the angle of view.

Note that, threshold level setter/water content index detector 27a may detect presence or absence of water at the irradiation position of reference beam LS1 and measuring beam LS2 of plant PT (refer to FIG. 5) according to a comparison of the size of rate RT of amplitude difference between amplitude VA of diffuse reflection light RV1 of reference beam LS1 and amplitude VB of diffuse reflection light RV2 of measuring beam LS2 (VA−VB) and amplitude VA with predetermined detection threshold level M.

Furthermore, threshold level setter/water content index detector 27a calculates an intensity rate of diffuse reflection light RV1 and diffuse reflection light RV2, that is, reflection intensity rate (also referred to as measurement value) Ln (I905/I1550) and obtains the water content index which is equivalent to water content that is contained in the leaf from the sum total of reflection intensity rate Ln (I905/I1550). Reflection intensity rate Ln (I905/I1550) is calculated, for example, in each predetermined pixel number (4×4 pixels) in all pixels in the frame image that is imaged by visible light camera VSC, and is expressed as reflection intensity rate W1 to Wk in each predetermined pixel number.

Memory 27b is configured using, for example, a random access memory (RAM), and temporarily stores output (peak information) of comparator/peak hold 25c in diffuse reflection light RV1 of reference beam LS1.

Detection result filter 27c filters and extracts information which relates to detection result of water from detection camera 1 based on output of threshold level setter/water content index detector 27a. Detection result filter 27c outputs information which relates to the extraction result to display processor 29. For example, detection result filter 27c outputs information which relates to the extraction result of water at the irradiation position of reference beam LS1 and measuring beam LS2 of plant PT to display processor 29.

Display processor 29 uses output of detection result filter 27c and generates detection result image data that indicates the position of water at the irradiation position at each distance from detection camera 1 as an example of information which relates to water at the irradiation position. Display processor 29 outputs detection result image data which includes information on distance from detection camera 1 to the irradiation position to display controller 37 of visible light camera VSC.

Next, each part of visible light camera VSC will be described. Imaging optics 31 is configured using, for example, a lens, ambient light RV0 from in the angle of view of detection camera 1 is concentrated, and ambient light RV0 forms an image on a predetermined imaging area of photo detector 33.

Photo detector 33 is an image sensor which has a peak of spectral sensitivity with respect to wavelength of visible light (for example, 0.4 to 0.7 μm). Photo detector 33 converts an optical image that forms an image on the imaging surface to the electrical signal. Output of photo detector 33 is input to image signal processor 35 as the electrical signal. Note that, imaging optics 31 and photo detector 33 function as an imaging unit in visible light camera VSC.

Image signal processor 35 uses the electrical signal which is output of photo detector 33, and visible light image data is generated which is specified by a person in recognizable red, green, and blue (RGB), brightness and color difference (YUV), and the like. Thereby, visible light image data that is imaged by visible light camera VSC forms visible light camera image data. Image signal processor 35 outputs visible light image data to display controller 37.

In a case where display controller 37 uses visible light image data that is output from image signal processor 35 and detection result image data that is output from display processor 29, and detects water at any position of the visible light image data, display data in which visible light image data and detection result image data are composited, or display data which comparatively represents the visible light image data and detection result image data are generated as examples of information related to water. Display controller 37 (output unit) prompts display by transmitting display data to data logger DL or communication terminal MT that are connected via, for example, a network.

Data logger DL transmits display data that is output from display controller 37 to communication terminal MT or one or more externally connected device, and prompts display of display data on a display screen of communication terminal MT or one or more externally connected device (for example, monitor 50 within the control room in the office indicated in FIG. 1).

Communication terminal MT is, for example, a portable communication terminal which is used by an individual user, receives display data that is transmitted from display controller 37 via the network, and displays display data on the display screen of communication terminal MT.

Figure 4:
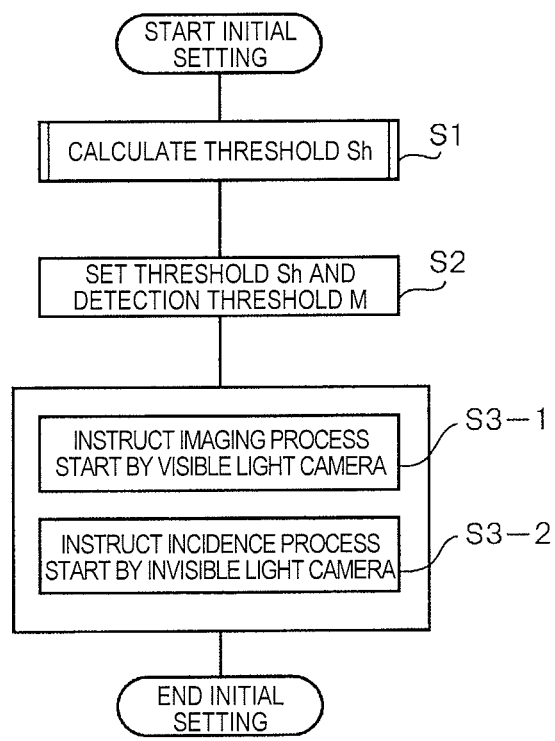
FIG. 4 is a flow chart illustrating an example of an initial operation in a controller of the detection camera.

Description of Example of Initial Operation in Invisible Light Sensor Controller Next, an example of an initial operation in controller 11 of invisible light sensor NVSS of detection camera 1 of the present embodiment will be described with reference to FIG. 4. FIG. 4 is a flow chart illustrating an example of an initial setting operation in controller 11 of detection camera 1.

When controller 11 instructs settings of threshold level Sh of reflection intensity rate for identifying the shape of the leaf with respect to threshold level setter/water content index detector 27a, threshold level setter/water content index detector 27a calculates and sets threshold level Sh (S1). Details of the process in which threshold level Sh is set will be described in detail. Note that, in a case where threshold level Sh is a fixed value, the process of step S1 may be omitted.

In addition, controller 11 sets detection threshold level M of water in detection processor 27 of invisible light sensor NVSS in threshold level setter/water content index detector 27a (S2). It is preferable to appropriately provide detection threshold level M according to a specific material that is a detection target.

After the process of step S2, controller 11 outputs a control signal for starting an imaging process to each part of visible light camera VSC (S3-1), and furthermore, outputs to first beam source 13 and second beam source 15 of invisible light sensor NVSS timing signal for beam scanning TR for starting incidence of reference beam LS1 and measuring beam LS2 to first beam source 13 and second beam source 15 (S3-2). Note that, either an execution timing of an operation of step S3-1 or an execution timing of an operation of step S3-2 may be first, or may be simultaneous.

Figure 5:
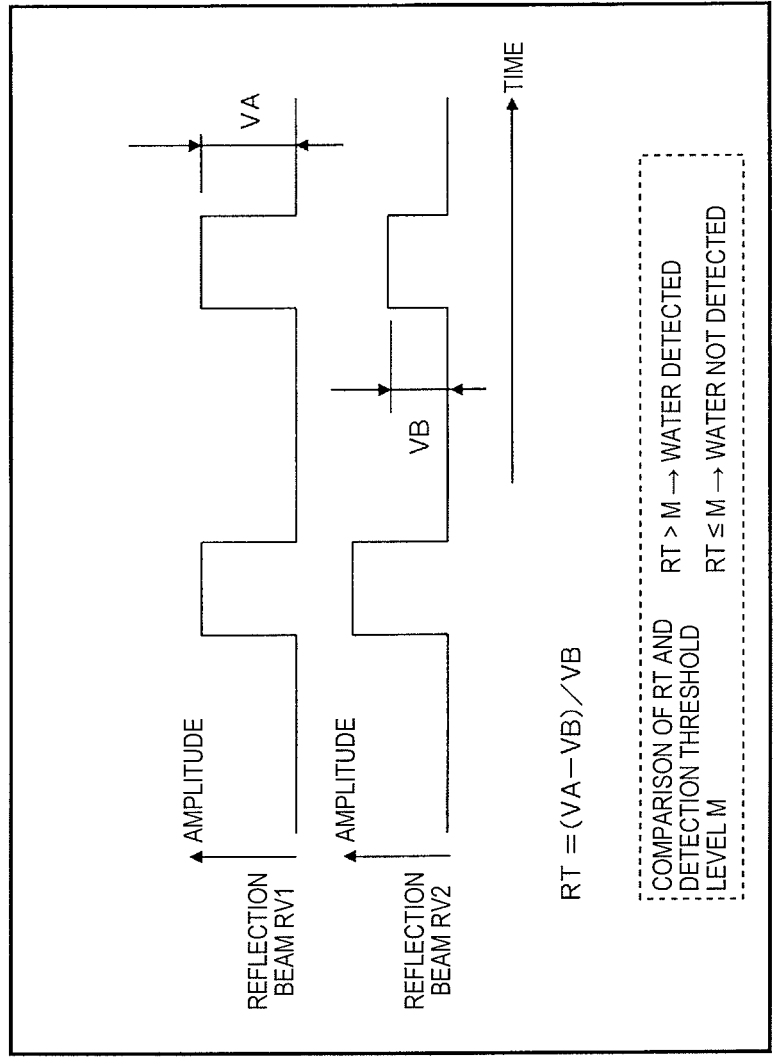
FIG. 5 is a principle explanatory diagram of detection of water in an invisible light sensor.

FIG. 5 is a principle explanatory diagram of detection of water in invisible light sensor NVSS. For example, threshold level setter/water content index detector 27a may determine that water is detected if RT>M, and may determine that water is not detected if RT≤M. In this manner, threshold level setter/water content index detector 27a is able to eliminate influence of noise (for example, disturbance light) and is able to detect presence or absence of water with high precision by detecting presence or absence of water according to a comparative result of rate RT between amplitude difference (VA−VB) and amplitude VA and detection threshold level M.

Figure 6:
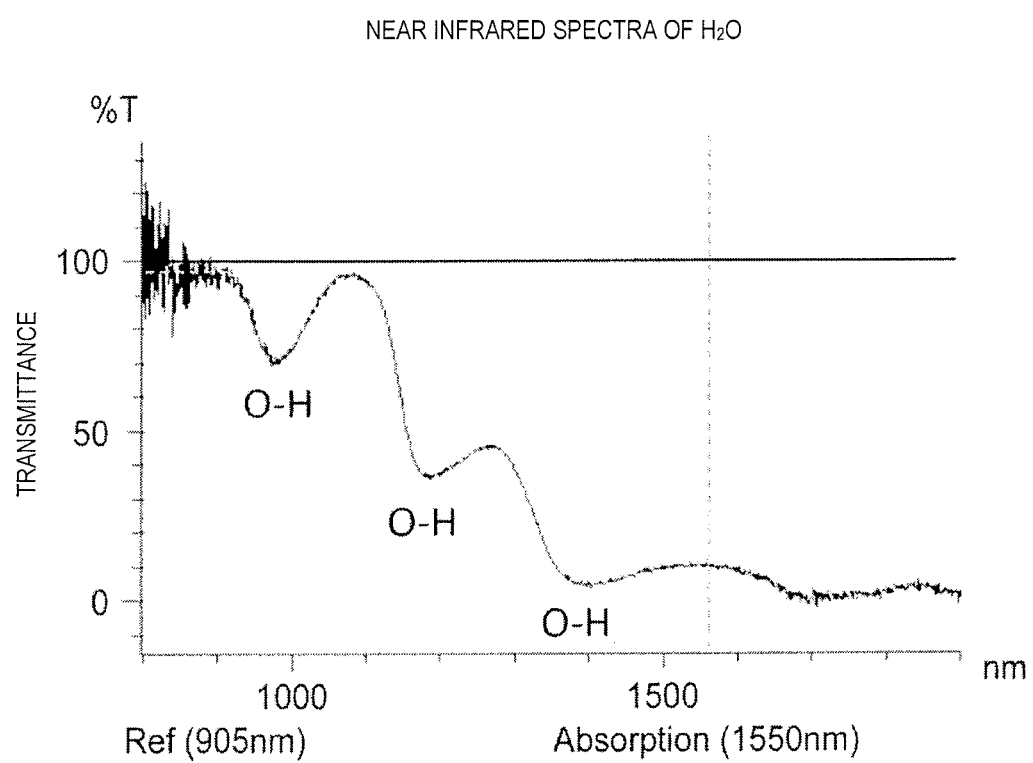
FIG. 6 is a graph illustrating a near infrared spectra of water ($H_2O$)

FIG. 6 is a graph illustrating the near infrared spectra of water ($H_2O$). A horizontal axis of FIG. 6 indicates wavelength (nm), and a vertical axis of FIG. 6 indicates transmittance (transparency) (%). As shown in FIG. 6, since reference beam LS1 of wavelength 905 nm has transmittance in water ($H_2O$) that is close to 100%, it is understood that reference beam LS1 has a characteristic of tending not to be absorbed in water. In the same manner, since measuring beam LS2 of wavelength 1550 nm has transmittance in water ($H_2O$) that is close to 10%, it is understood that measuring beam LS2 has a characteristic of tending to be absorbed in water. Therefore, in the present embodiment, the wavelength of reference beam LS1 which is incident from first beam source 13 is 905 nm, and the wavelength of measuring beam LS2 which is incident from second beam source 15 is 1550 nm.

FIG. 7A is a diagram which describes a summary of an operation which measures the reflection intensity rate of the entirety of the leaf. An irradiation range of the near infrared beam is set in a range so as to include the entirety of the front surface of the leaf. A light absorption amount of the near infrared beam (measuring beam) is reflected in a reflection intensity rate using water in which there is up to a depth of approximately tens of p in a thickness direction of the leaf.

In a case where a projection range of the near infrared beam is reduced due to the leaf having withered, even in a case where the thickness of the leaf increases due to the leaf bending or coiling, in the present embodiment, a total sum of the reflection intensity rate (hereinafter referred to as a water content index) in all pixels of the leaf is set as an index of water content. Accordingly, the water content index is represented by $\Sigma$ Ln (I905/I1550), and has correlation with water potential.

FIG. 7B is a diagram which describes a summary of an operation which measures the reflection intensity rate in which a spot is in a fixed area. As described above, even if water content per unit area is obtained by radiating while sequentially scanning the near infrared beam within a smaller range than the front surface of the leaf, correlation between the water content per unit area and water potential is low.

Figure 8:
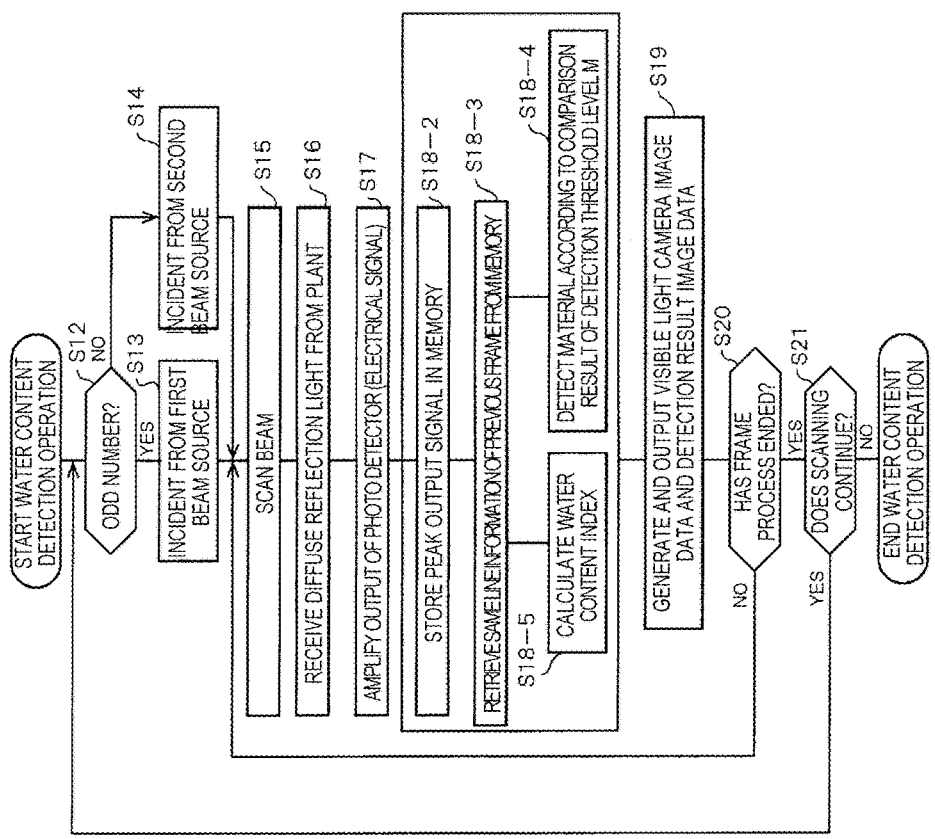
FIG. 8 is a flow chart illustrating a detailed operation procedure which relates to detection of water content of a leaf or a part of plant in the invisible light sensor.

Description of Detailed Operation Relating to Detection of Water or Undulation of Invisible Light Sensor Next, a detailed operation procedure which relates to detection of water in invisible light sensor NVSS of detection camera 1 will be described with reference to FIG. 8. FIG. 8 is a flow chart illustrating a detailed operation procedure which relates to detection of water that is contained in leaf PT3 of plant PT in invisible light sensor NVSS. As a premise of description of the flow chart illustrated in FIG. 8; timing controller 11a outputs timing signal for beam scanning TR to first beam source 13 and second beam source 15, and reference beam LS1 and measuring beam LS2 from detection camera 1 is radiated toward leaf PT3 of plant PT.

In FIG. 8, controller 11 determines whether or not beam output signal RF in incidence period of an odd number of times is output from timing controller 11a (S12). In a case where controller 11 determines that beam output signal RF in incidence period of an odd number of times is output from timing controller 11a (S12, YES), first beam source 13 incidents reference beam LS1 according to beam output signal RF from timing controller 11a (S13). Beam scanner 17 one-dimensionally scans reference beam LS1 of one line or more in an X direction of plant PT which is contained in the angle of view of detection camera 1 (S15). At the irradiation position on each line in the X direction on which the reference beam LS1 is radiated, diffuse reflection light RV1 that is generated by reference beam LS1 being diffused and reflected is received by photo detector 23 via imaging optics 21 (S16).

In signal processor 25, output (electrical signal) in photo detector 23 of diffuse reflection light RV1 is converted to the voltage signal, and the level of the electrical signal is amplified up to a processable level in comparator/peak hold 25c (S17). Comparator/peak hold 25c binarizes the output signal of amplifier 25b and outputs to threshold level setter/water content index detector 27a according to a comparative result of the output signal of amplifier 25b and the predetermined threshold level. Comparator/peak hold 25c outputs peak information of output signal of amplifier 25b to threshold level setter/water content index detector 27a.

Threshold level setter/water content index detector 27a temporarily stores output (peak information) of comparator/peak hold 25c with respect to diffuse reflection light RV1 of reference beam LS1 in memory 27b (S18-2). In addition, threshold level setter/water content index detector 27a reads from memory 27b output of comparator/peak hold 25c with respect to the same line in diffuse reflection light RV1 or diffuse reflection light RV2 with respect to reference beam LS1 or measuring beam LS2 in a previous frame (incidence period) that is stored in memory 27b (S18-3).

Threshold level setter/water content index detector 27a detects presence or absence of water on the same line based on output (peak information) of comparator/peak hold 25c in diffuse reflection light RV1 of reference beam LS1 and output (peak information) of comparator/peak hold 25c in diffuse reflection light RV2 of measuring beam LS2 on the same line and predetermined detection threshold level M (S18-4).

Threshold level setter/water content index detector 27a calculates the water content index which is total sum $\Sigma$ Ln (I905/I1550) of the reflection intensity rate (S18-5). Details of calculation of the water content index will be described in detail.

Display processor 29 uses output of detection result filter 27c and generates detection result image data that indicates the detection position of water. Display controller 37 outputs detection result image data that is generated by display processor 29 and visible light camera image data of a visible light image that is imaged by visible light camera VSC (S19). Each operation of steps S15, S16, S17, S18-2 to S18-5, and S19 is executed in each line within the detection area of one frame (incidence period).

That is, when each operation of steps S15, S16, S17, S18-2 to S18-5, and S19 is complete with respect to one line in the X direction, each operation of steps S15, S16, S17, S18-2 to S18-5, and S19 is performed with respect to a subsequent line in the X direction (S20, NO), hereinafter until each operation of steps S15, S16, S17, S18-2 to S18-5, and S19 is complete in one frame, each operation of steps S15, S16, S17, S18-2 to S18-5, and S19 is repeated with respect to scanning in a Y direction indicated in enlarged diagram EPG in FIGS. 7A and 7B.

Meanwhile, in a case where execution of each operation of steps S15, S16, S17, S18-2 to S18-5, and S19 is complete with respect to all lines in one frame (S20, YES), and in a case where scanning of incident light is continued (S21, YES), an operation of invisible light sensor NVSS returns to step S12. Meanwhile, in a case where scanning of reference beam LS1 and measuring beam LS2 is not continued (S21, NO), the operation of invisible light sensor NVSS is complete.

Figure 9:
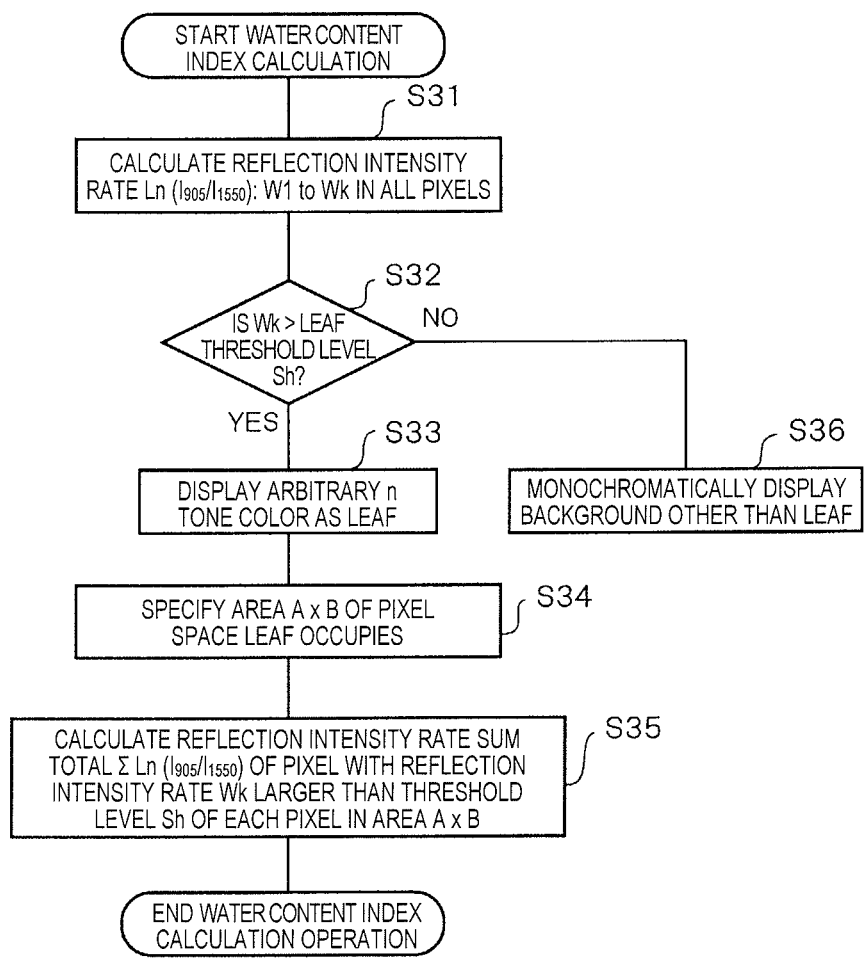
FIG. 9 is a flow chart illustrating a calculation procedure of a water content index in step S18-5.

FIG. 9 is a flow chart illustrating a calculation procedure of a water content index in step S18-5. Threshold level setter/water content index detector 27a calculates reflection intensity rate Ln (I905/I1550) in all pixels from the frame image (S31). Here, a measurement value of reflection intensity rate Ln (I905/I1550) of each pixel is represented by reflection intensity rates W1 to Wk. For example, in a case where the image of the near infrared beam is configured from 76,800 (=320×240) pixels, a suffix k of Wk is a variable which represents 1 to 76,800.

Threshold level setter/water content index detector 27a determines whether or not the reflection intensity rate Wk of each pixel is larger than threshold level Sh for identifying leaf PT3 (S32). An initial value of threshold level Sh is registered in advance in threshold level setter/water content index detector 27a as an empirical value. The empirical value is determined according to a specification of the water content evaluation apparatus (intensity of the irradiation laser beam, sensitivity of a light receiving element, and the like), water content (about 90%) of the leaf that is the measurement target, thickness of the leaf (for example, 200 μm), inside/outside (or "indoor/outdoor"), and the like. In particular, in a case of outside, there is change according to how sunlight hits or manner of growth of foliage, and the variable is changed each time.

For example, as the empirical value, in the case of an imaging distance of 1 m, threshold level Sh during imaging inside is set to approximately 0.3. Threshold level Sh during imaging outside is set to approximately 0.9. In addition, in the case of an imaging distance of 3 m, threshold level Sh during imaging inside is set to approximately 0.05. It is preferable to change threshold level Sh in a case where threshold level Sh is set as the initial value, it is determined whether or not the threshold level is optimal in comparison to the actual shape of the leaf, and the threshold level is not optimal. In addition, as will be described later, a calculation process of threshold level Sh is performed, and it is possible to register calculated threshold level Sh as the initial value.

In step S32, in a case where reflection intensity rate Wk is less than threshold level Sh, the pixel is a pixel that represents a background other than the leaf, and display processor 29 generates monochromatic display data for displaying pixels monochromatically (S36).

Meanwhile, in step S32, in a case where reflection intensity rate Wk is threshold level Sh or more (threshold level or more), display processor 29 displays pixels in a tone color corresponding to reflection intensity rate Ln (I905/I1550) (S33). Here, it is possible to display the tone color corresponding to reflection intensity rate Ln (I905/I1550) at n tone. n is an arbitrary positive number. FIG. 10 is a table illustrating a tone color corresponding to the reflection intensity rate. Reflection intensity rate Ln (I905/I1550) and an intensity ratio (reflection light of 905 nm/reflection light of 1550 nm) are classified in each gradation color in table Tb.

In detail, in a case where reflection intensity rate Ln (I905/I1550) is less than 0.3, that is, in a case of being threshold level Sh of the leaf or less, the pixel is displayed using, for example, white (monochrome). Meanwhile, in a case where reflection intensity rate Ln (I905/I1550) is 0.3 to less than 0.4, the pixel is displayed using, for example, dark green. In the same manner, in a case of being 0.4 to less than 0.5, the pixel is displayed using green. In a case of being 0.5 to less than 0.55, the pixel is displayed using yellow. In a case of being 0.55 to less than 0.6, the pixel is displayed using orange. In a case of being 0.6 to less than 0.75, the pixel is displayed using red. In a case of being 0.75 or more, the pixel is displayed using purple. In this manner, the color of the pixel that belongs to the leaf is set in any of six tones.

Note that, in a case where a pixel space which the leaf occupies is not appropriate in comparison to the actual shape of the leaf, the user may set threshold level Sh up or down in each predetermined increment (for example, 0.01). Alternatively, the user may set appropriate threshold level Sh by activating a process (refer to FIG. 13) in which threshold level Sh described later is automatically set.

Threshold level setter/water content index detector 27a specifies an area of the pixel space which the leaf occupies (S34). FIG. 11 is a table illustrating the reflection intensity rate in a portion of a frame image which includes a pixel space that the leaf occupies. As a portion of the frame image, reflection intensity rate Ln (I905/I1550) of 21 pixels×9 pixels is indicated in the table. The pixels where the background is green (dot display) is equivalent to pixels of the leaf. As described above, pixels of the leaf are pixels in which reflection intensity rate Ln (I905/I1550) exceeds threshold level Sh (here, 0.3). In addition, an area ARE of a rectangle (A×B) is specified such that the pixels of the leaf are enclosed. The area ARE is used as a value which determines the size of the leaf. Note that, the size of the leaf may represent the pixel number which exceeds threshold level Sh.

Threshold level setter/water content index detector 27a (water content calculation unit) calculates water content index $\Sigma$ Ln (I905/I1550) that is a sum total of reflection intensity rate Ln (I905/I1550) where a measurement value (reflection intensity rate Ln (I905/I1550)) is larger than threshold level Sh in area ARE (S35). Water content which is contained in the entirety of the leaf is understood by obtaining water content index $\Sigma$ Ln (I905/I1550).

Furthermore, in step S35, it is possible for threshold level setter/water content index detector 27a to calculate the number of pixels in which the measurement value (reflection intensity rate Ln (I905/I1550)) is larger than threshold level Sh in area ARE, and calculate an average value by dividing total sum $\Sigma$ Ln (I905/I1550) of the reflection intensity rate by the number of calculated pixels. The average value is a value in which the total sum of the reflection intensity rate is divided by the area of the leaf where the external form of the leaf is determined by threshold level Sh, and a value in which the total sum of the reflection intensity rate in a spot is divided by a fixed area of the spot and a value in which the total sum of the reflection intensity rate is divided by the area that is enclosed by the external form of the leaf in the visible image are different. After this, the calculation operation of the water content index ends.

In this manner, in the present embodiment, the reflection intensity rate of each irradiation position is not obtained, the reflection intensity rate of each pixel in the frame image is obtained, and it is possible to correctly calculate the water content index from the total sum of reflection intensity rate of each pixel. Accordingly, it is possible to accurately determine status of the leaf, that is, the plant.

Figure 12A:
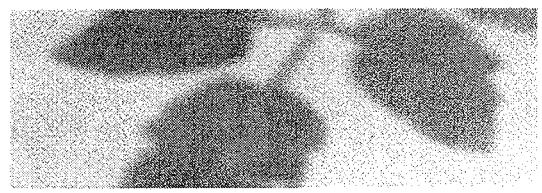
FIG. 12A is a frame image that images stalks and leaves of a tomato.
Figure 12B:
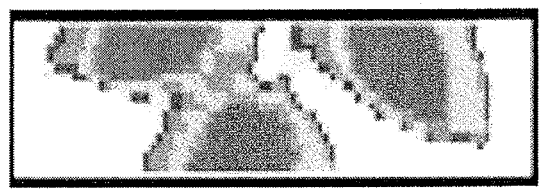
FIG. 12B is a diagram illustrating an occupancy space of the leaf that is obtained in a case where an imaging distance is set to 3 m and a threshold level is set to 0.05 with respect to the visible light image of FIG. 12A.
Figure 12C:
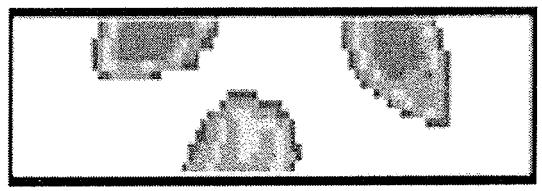
FIG. 12C is a diagram illustrating an occupancy space of the leaf which is obtained in a case where the imaging distance is set to 1 m and the threshold level is set to 0.3 with respect to the visible light image of FIG. 12A.

Here, as described above, threshold level Sh of the leaf is set to a subsequent value as the initial value. In a case where detection camera 1 is installed inside and leaf PT3 is imaged inside, and in a case where imaging distance is empirically 1 m, threshold level Sh is set to approximately 0.3. In the case of an imaging distance of 3 m, threshold level Sh is set to approximately 0.05. Meanwhile, in a case of imaging outside, since a condition of sunlight varies, threshold level Sh is empirically set to approximately 0.9. FIGS. 12A to 12C are diagrams illustrating an occupancy range of the leaf. FIG. 12A is a frame image that images stalks and leaves of a tomato. A distance between leaves is approximately 1 cm. FIG. 12B illustrates the occupancy space of the leaf which is obtained in a case where the imaging distance is set to 3 m and threshold level Sh is set to 0.05 with respect to the visible light image in FIG. 12A. In this case, it is understood that the leaves overlap in portions and threshold level Sh (=0.05) is a value that is inappropriately set. FIG. 12C illustrates the occupancy space of the leaf which is obtained in a case where the imaging distance is set to 1 m and threshold level Sh is set to 0.3 with respect to the visible light image in FIG. 12A. In this case, the outer form of the leaf does not overlap with another leaf, in addition, the occupancy space of the leaf is the same as the size of the outer form of the leaf of the visible light image. In this case, it is understood that threshold level Sh (=0.3) is a value that is correctly set.

Figure 13:
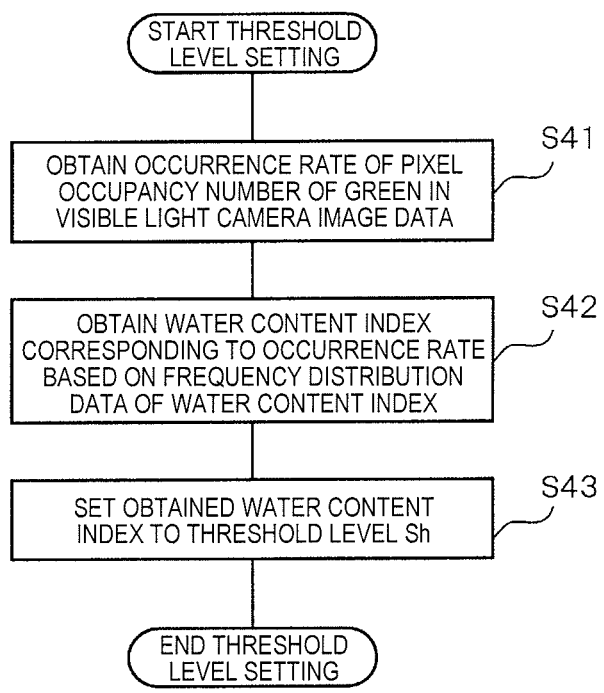
FIG. 13 is a flow chart illustrating a threshold level setting procedure.

In addition, threshold level Sh of the leaf may not be registered before the subsequent process is performed and the calculation process of the water content index indicated in FIG. 9 is executed. FIG. 13 is a flow chart illustrating a threshold level setting procedure.

Threshold level setter/water content index detector 27a obtains an occupancy rate that is determined as the leaf (G pixel number/all pixel numbers), i.e. a pixel occupancy of green (G) that is determined as the color of the leaf with respect to the frame image (for example, refer to FIG. 12A) that is imaged by visible light camera VSC (S41).

Figure 14:
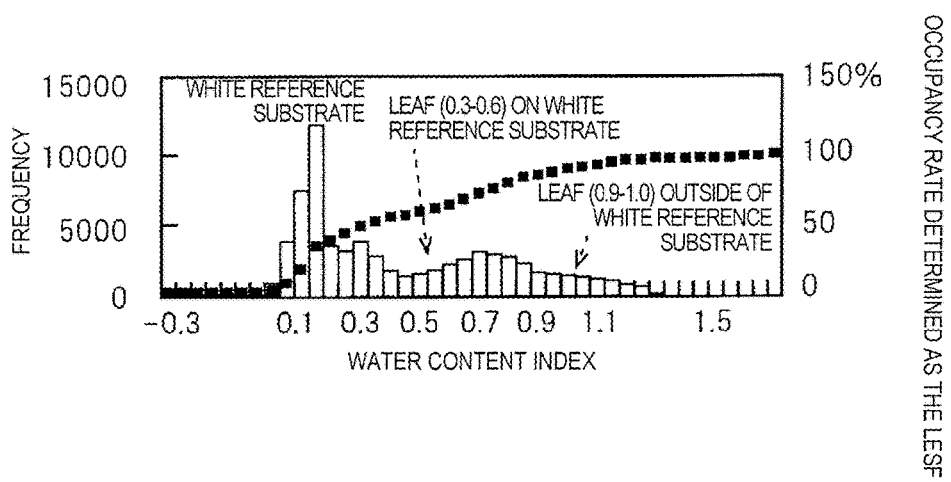
FIG. 14 is a graph illustrating a frequency distribution of the reflection intensity rate in all pixels.

Threshold level setter/water content index detector 27a obtains the water index corresponding to the occupancy rate of the leaf based on frequency distribution data of the water content index (S42). FIG. 14 is a graph illustrating the frequency distribution of the reflection intensity rate in all pixels. Frequency distribution data is registered in threshold level setter/water content index detector 27a. When using the frequency distribution data, in a case where, for example, the occupancy rate of the leaf is 52%, the water content index is approximately 0.3.

Threshold level setter/water content index detector 27a sets the water content index that is obtained in step S42 to threshold level Sh (S43). After this, threshold level setter/water content index detector 27a ends the present process.

In this manner, it is possible to correctly determine the outer form of the leaf by obtaining an occupancy pixel number of green (specified color) of the leaf and threshold level Sh corresponding to cumulative frequency of Ln (I905/I1550) that is the measurement value which is the same pixel number by utilizing the visible light image that is imaged by visible light camera VSC, that is, by modifying the threshold level of the water content of each pixel that is contained in the leaf. Accordingly, it is possible to accurately calculate the average value of the pixel unit by correctly determining the outer form of the leaf. In contrast to this, in a case where the fixed area of the spot or the outer form of the visible light image is used, when the outer form of the leaf is not correctly captured, a large error is generated in the average value of the pixel unit.

In FIGS. 4 to 14, water content of the leaf is calculated based on the pixel with a part that is determined to be the outer form of the leaf being set as the outer form of the leaf and has a higher water content than the outer form of the leaf by setting the one threshold level of water content. However, the water content of the leaf may be calculated using the threshold level for determining the outer form of the leaf and a plurality of threshold levels compiled from other threshold levels. For example, another threshold level may be set in order to exclude the pixel which is equivalent to a leaf vein, and in particular, a main vein from the calculation target of the water content of all leaves. The leaf vein is a transportation route for water or nourishment. Therefore, even if water content of all leaves reduces, the water content of, for example, the leaf vein, and in particular, the main vein tends not to relatively reduce more than another part. Furthermore, since an incidence direction of sunlight with respect to the leaf changes with time, the threshold level may be set to a different value according to the measurement time.

Figure 15A:
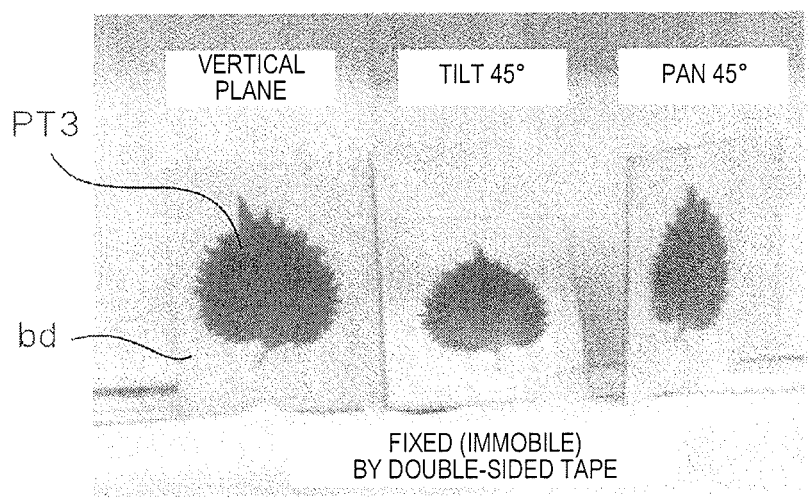
FIG. 15A is a diagram illustrating the leaf that is fixed in various postures during measurement.

FIG. 15A is a diagram illustrating the leaf that is fixed in various postures during measurement. In water measurement of the leaf, white reference substrate bd is prepared as a plate material that has a flat surface, and leaf PT3 is affixed using double-sided tape such that the rear surface of leaf PT3 overlaps with the surface of the plate material. In first water measurement, the plate material is set so as to be a vertical plane with respect to an optical axis of detection camera 1. In second water measurement, the plate material is set so as to be inclined at a tilt angle of 45° with respect to the optical axis of detection camera 1. In third water measurement, the plate material is set so as to be inclined at a pan angle of 45° with respect to the optical axis of detection camera 1.

Figure 15B:
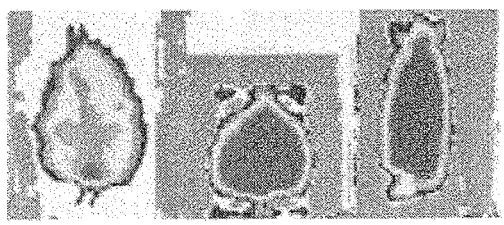
FIG. 15B is a diagram illustrating an image which represents the reflection intensity rate of the leaf.

FIG. 15B is a diagram illustrating an image which represents the reflection intensity rate of the leaf. In first water measurement, the area in which the reflection intensity rate exceeds threshold level Sh is close to the outer form of the leaf viewed from a front surface. In addition, it is understood that the reflection intensity rate in the center of the leaf maximally increases from the inside of the leaf and the reflection intensity rate gradually lowers. In second water measurement, the area in which the reflection intensity rate exceeds threshold level Sh is close to the outer form of the leaf with the leaf viewed inclined in the tilt direction. In addition, the reflection intensity rate is high across a wide range inside the leaf. The thickness of the leaf increases in the optical axis direction due to the leaf tilting with respect to the optical axis, and as apparent, is considered to be due to water content of the leaf becoming great. In third water measurement, the area in which the reflection intensity rate exceeds threshold level Sh is close to the outer form of the leaf with the leaf viewed inclined in the pan direction. In addition, the reflection intensity rate is high across a wide range inside the leaf. In the same manner as the case of the second water measurement, the thickness of the leaf increases in the optical axis direction due to the leaf tilting with respect to the optical axis, and as apparent, is considered to be due to water content of the leaf becoming great.

Figure 16:
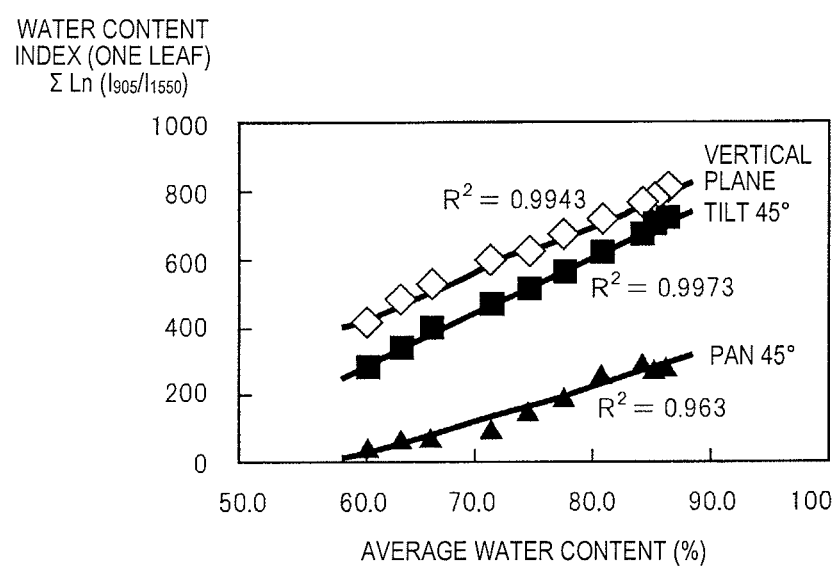
FIG. 16 is a graph illustrating the reflection intensity rate with respect to average content.

FIG. 16 is a graph illustrating the reflection intensity rate with respect to an average content. According to the graph, in the total sum (water content index) of the reflection intensity rates that are respectively obtained in first, second, and third water content measurement, the larger an average water content of the leaf, the larger the value becomes, and there is a high correlation with respect to the average water content. In first water content measurement, square ($R2$) of correlation coefficient is 0.9943. In second water' content measurement, square ($R2$) of correlation coefficient is 0.9973. In third water content measurement, square ($R2$) of correlation coefficient is 0.963. In this manner, in the case of any water content measurement, the water content index has high correlation with respect to the average water content.

Figure 17A:
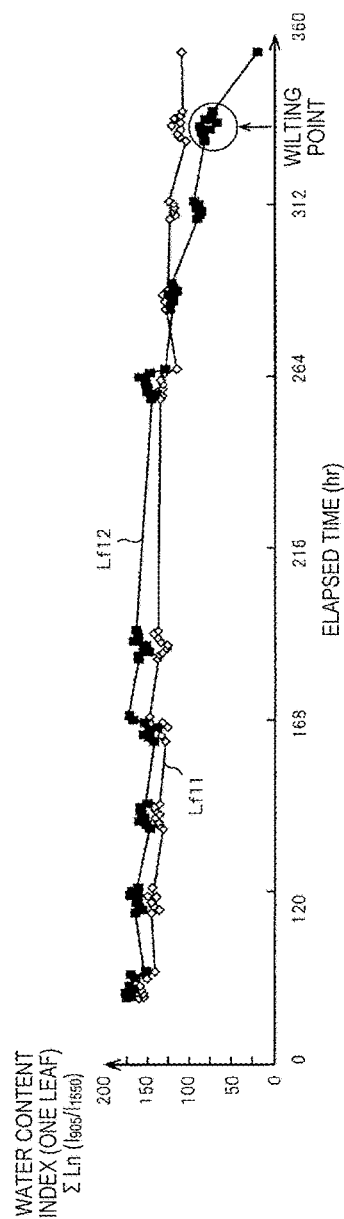
FIG. 17A is a graph illustrating a wilting process of the plant.

Next, a tomato seedling is used, and a wilting process and root water absorption (revival) process are indicated after irrigation stops (suspension of water supply). FIG. 17A is a graph illustrating a wilting process of the plant. The vertical axis indicates the water content index of one leaf ($=\Sigma$ Ln (I905/I1550)), and the horizontal axis indicates an elapsed time from the start of suspension of water supply. Curve Lf11 indicates the water content index of the leaf with reference to a case where irrigation is performed two times, morning and evening, in one day. Curve Lf12 indicates a case in which irrigation is not performed again after a wilting point is reached in a case where the irrigation is stopped (water supply is suspended). In addition, in FIG. 17A, in various marks of curve Lf11 and curve Lf12, the start of the marks indicate around 9 am and the end of the marks indicate around 5 μm, and a mass of the number of the various marks indicate a range from around 9 am until around 5 μm in one day.

When the average water content of the leaf gradually reduces from 86% while exceeding the time of the water supply suspension time and water supply suspension time exceeds 330 hours, the wilting point of water content 50% or less is reached. In the leaf in a case where water supply is not suspended, and irrigation is performed every day regularly twice, in the morning and evening, as indicated in curve Lf11, the average water content of the leaf is maintained at substantially the same value (water content index: value 110) as the measurement initialization. Meanwhile, in the leaf in which water supply continues to be suspended, as apparent, when average water content of the leaf continues to lower after the wilting point at which stalks and leaves wilt and the water supply suspension time is 350 hours, the water content index is lowered to a value 20.

Figure 17B:
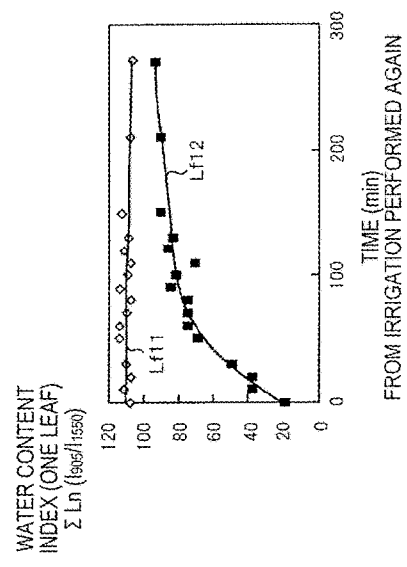
FIG. 17B is a graph illustrating a revival process.

FIG. 17B is a graph illustrating a revival process. After the water content index of the leaf lowers to the value 20, when irrigation is performed again, the average water content of the leaf gradually raises along with elapsing of the time after irrigation is performed again. When the elapsed time reaches 280 minutes, the average water content of the leaf to which water supply is suspended reaches a value (water content index: 100) close to the average water content of the leaf prior to the water supply being suspended.

Figure 18:
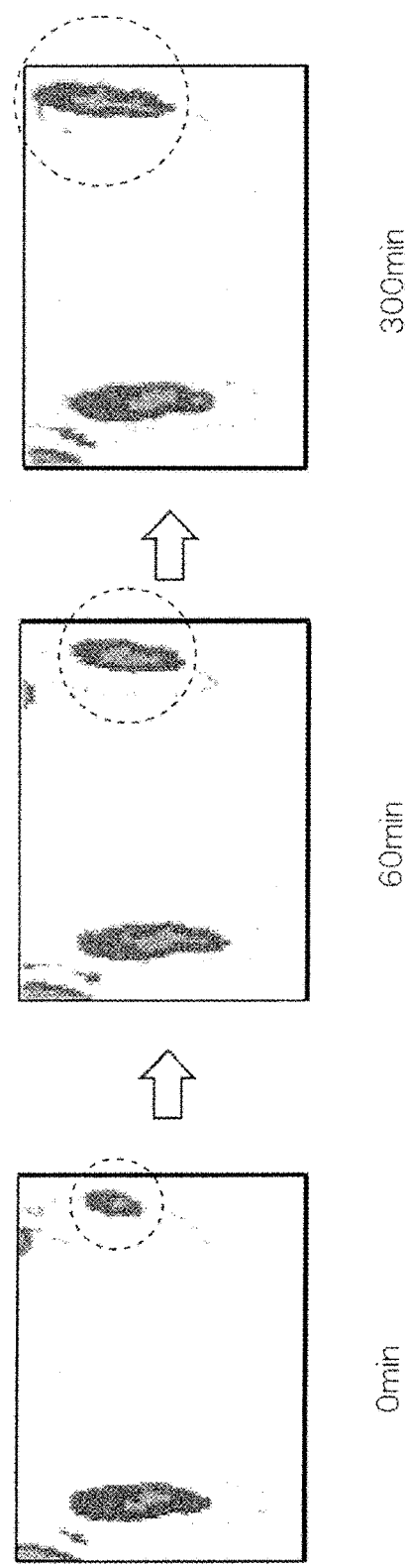
FIG. 18 is a diagram illustrating a process in which water content of the leaf that approaches wilting gradually increases.

FIG. 18 illustrates a process in which water content of the leaf that approaches wilting gradually increases using actual measurement data (diagram in which a reflection intensity rate table of a frame image displays tone) used when the graph of the revival process in FIG. 17B is plotted. In a case where the elapsed time from performing irrigation again is 0 minutes, when the area of the leaf in which reflection intensity rate Ln (I905/I1550) exceeds threshold level Sh is small and 60 minutes elapse, there is a slight increase, and when 300 minutes elapse, there is a further increase. Then, it is understood that the water content of the leaf is revived until an equal level as when irrigation is regularly performed in the morning and evening where the water supply is not suspended (left side leaves of each frame images in the diagram equivalent to curve Lf11 in FIG. 17B).

In this manner, it is possible to visually grasp the wilting process and the root water absorption (revival) process by measuring the water content which is contained in the leaf.

Comparative Example

Figure 19:
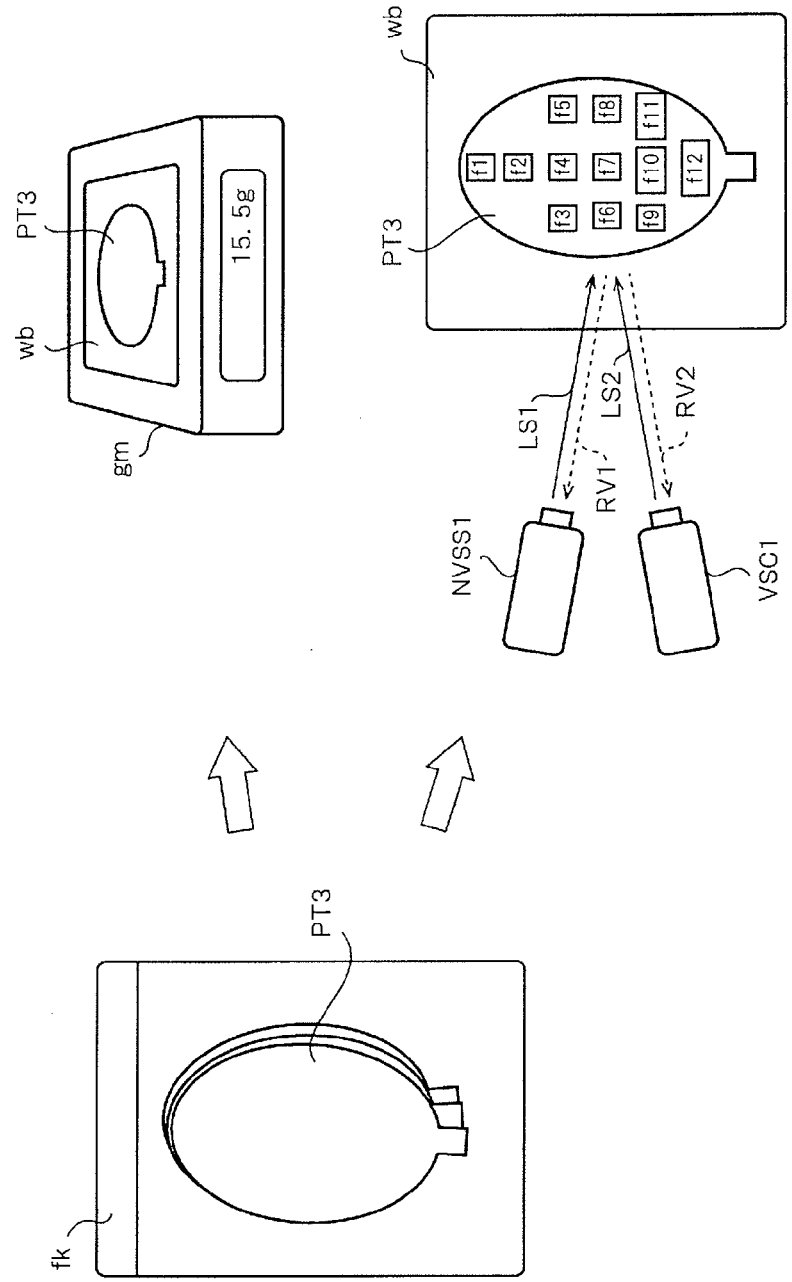
FIG. 19 is a diagram which describes a measurement method of a comparative example.
Figure 20A:
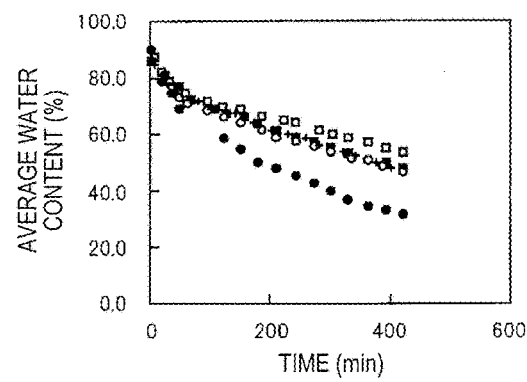
FIG. 20A is a graph illustrating a time change of weight of the leaf due to transpiration, that is, a time change of average water content of the leaf.

FIG. 19 is a diagram which describes a measurement method of a comparative example. Macrophyll leaf PT3 that is sealed and packed in vinyl bag fk is taken out and fixed to white board wb such that leaf PT3 does not move. White board wb that is firmly fixed to leaf PT3 is placed on weight scale gm, and the weight is measured. At this time, since the weight of white board wb is measured in advance, and is adjusted by 0 points, the weight of the leaf is displayed on a meter of weight scale gm. Change of weight due to transpiration of the leaf is measured while the time elapses. After all measurement ends, the leaf completely dries and the weight is obtained. The average water content of the leaf during measurement is obtained by deducting the weight of the leaf during drying from the weight of the leaf during measurement. FIG. 20A is a graph illustrating a time change of weight of the leaf due to transpiration, that is, time change of average water content of the leaf. The average water content substantially lowers while the time elapses.

Figure 20B:
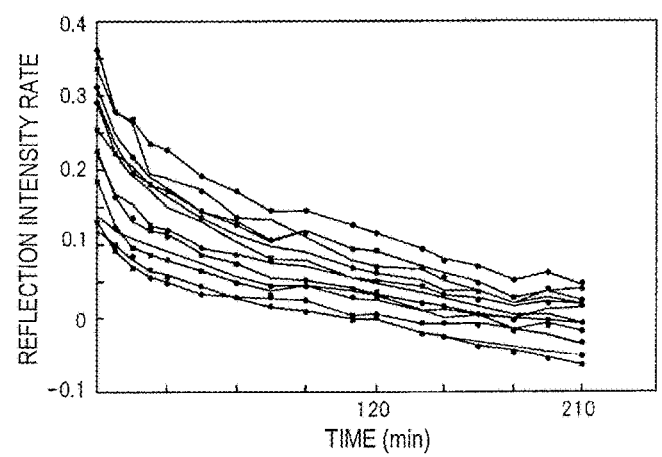
FIG. 20B is a graph illustrating a time change of reflection intensity rate Ln (I905/I1550) that is measured at 12 locations on the leaf.

In addition, white board wb to which leaf PT3 is fixed is placed in a standing state. In this state, visible light camera VSC1 images the leaf. Furthermore, invisible light camera NVSS1 respectively radiates the near infrared beam which has a wavelength of 905 nm and a wavelength of 1550 nm with respect to 12 locations on the leaf, and reflection intensity rate Ln (I905/I1550) is measured. The 12 locations on the leaf are areas that are set across the entire leaf, and have a size of 4×4 pixels. FIG. 20B is a graph illustrating time change of reflection intensity rate Ln (I905/I1550) that is measured at 12 locations on the leaf.

Figure 20C:
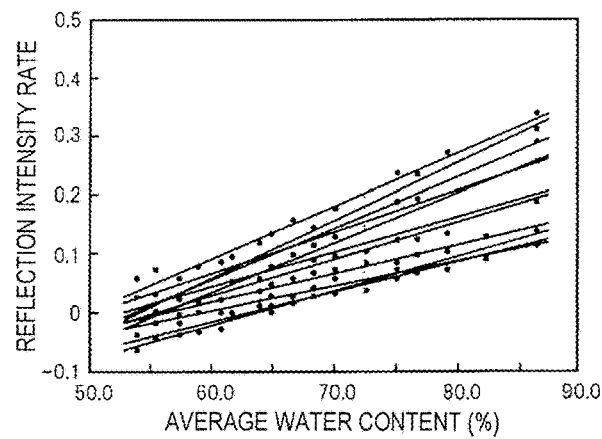
FIG. 20C is a graph which is obtained based on measurement data of FIGS. 20A and 20B, and illustrating a correspondence relationship of reflection intensity rate Ln (I905/I1550) and the average water content.

FIG. 20C is a graph which is obtained based on measurement data of FIGS. 20A and 20B, and illustrating a correspondence relationship of reflection intensity rate Ln (I905/I1550) and the average water content. At any of the 12 locations on the leaf, there is a proportional relationship of reflection intensity rate Ln (I905/I1550) and the average water content. Accordingly, in a case where the leaf is firmly fixed so as not to move, the average water content on the leaf is understood by measuring reflection intensity rate Ln (I905/I1550).

In this manner, in the water content evaluation apparatus in the first embodiment, first beam source 13 of detection camera 1 radiates the near infrared beam (reference beam) of first wavelength (905 nm) that has a characteristic of tending not to be absorbed in water toward leaf PT3 of plant PT by optical scanning. Second beam source 15 of detection camera 1 radiates the near infrared beam (measuring beam) of second wavelength (1550 nm) that has a characteristic of tending to be absorbed in water toward leaf PT3 of plant PT by optical scanning. Threshold level setter/water content index detector 27a calculates the water content index of one leaf that is total sum Σ Ln (I905/I1550) of reflection intensity rate based on a reflection light of 905 nm on all irradiation positions of leaf PT3 and a reflection light of 1550 nm on all irradiation positions of leaf PT3. Therefore, it is possible to accurately measure water content which is contained in the plant that is the index of status of the plant.

In addition, threshold level setter/water content index detector 27a holds threshold level Sh which indicates the water content and identifies the shape of one plant, and adds water content in at least one irradiation position that is threshold level Sh or more. Thereby, it is possible to appropriately calculate water content of the plant using threshold level Sh.

In addition, visible light camera VSC acquires the visible light image of the plant, and threshold level setter/water content index detector 27a calculates threshold level Sh using the visible light image of the acquired image. Thereby, it is possible to set threshold level Sh which is able to correctly identify the shape of the plant.

In addition, display controller 37 outputs at least one invisible light image out of leaf, seed, stalk, and flower of the plant. Thereby, it is possible to confirm whether or not the shape of the plant is correct according to the output invisible light image.

In addition, threshold level setter/water content index detector 27a calculates water content at each irradiation position, and calculates the water content at all irradiation positions of the plant by adding the calculated water content. Display controller 37 displays the invisible light image in steps to be identifiable according to the water content which is calculated at each irradiation position. Thereby, it is possible to visually recognize the distribution of water content which is contained in the plant other than the water content of the entire plant.

In addition, each irradiation position corresponds to a pixel of a predetermined number in the invisible light image. Thereby, it is possible to associate the position of the plant and the position of the invisible light image.

Details and Problems of Second Embodiment

In a case where the front surface of the leaf of the plant is irradiated with two types of near infrared beam and water from the reflection intensity rate is obtained, there is the following problem. When measuring by radiating the near infrared beam, the near infrared beam (for example, pulsed light) is radiated on the leaf that is the measurement target, and the part of the light which is diffused and reflected in all directions on the front surface of the leaf is received and measured in a detection unit for the near infrared light by slightly shifting the irradiation timing (for example, by shifting a p SEC order). In addition, the light radiated here is the laser beam, therefore the wavelength width is narrow by only a wavelength at the unit wavelengths of 905 nm and 1550 nm. Furthermore, the detection unit for the near infrared light is not for the unit wavelength (a filter through which only 905 nm and 1550 nm pass or the like which is not attached), and is a photoelectric converter (photosensor) which electrically changes light of a near infrared light region of a wide range.

Figure 22A:
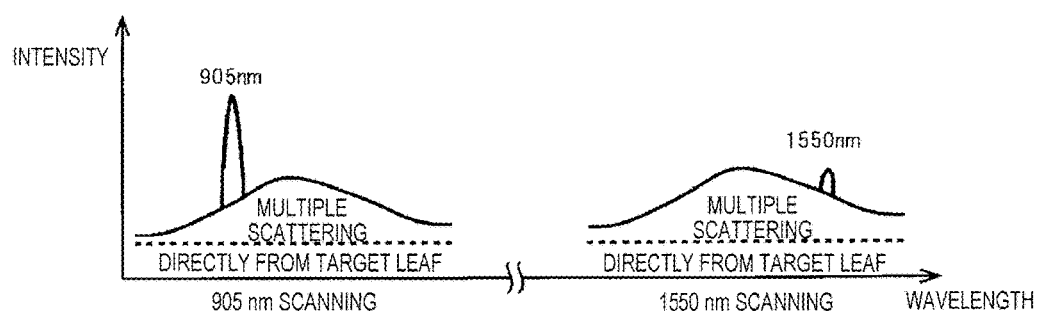
FIG. 22A is a graph illustrating a reflection light intensity with respect to a wavelength of a near infrared beam when near infrared beam is radiated toward the leaf outdoors.

Here, there is a problem when receiving light in the detection unit of the near infrared light, but there is sunlight that is external light. Sunlight has a wide wavelength area different from the laser beam, and has any wavelength in the near infrared light area. Sunlight is divided into "directly reflected light" in which a part of sunlight is directly reflected at the leaf that is the measurement target and "multiple scattering light" which is subjected to multiple scattering between peripheral leaves as indicated in FIG. 22A. Then, such that the timing of both during radiation of the near infrared beam of 905 nm and during radiation of the near infrared beam of 1550 nm are the same, the reflection intensity rate of 905 nm/1550 nm is significantly raised by the near field spectra indicated in FIG. 6. So, when there is a significant rise in the background, it is difficult to distinguish individual measurement target leaves and peripheral leaves.

Figure 21A:
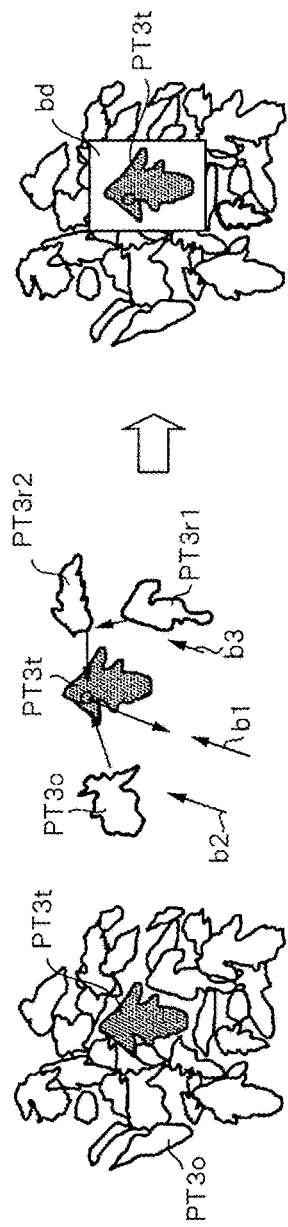
FIG. 21A is a diagram which describes a summary of an operation of a water content evaluation apparatus in a second embodiment.
Figure 21B:
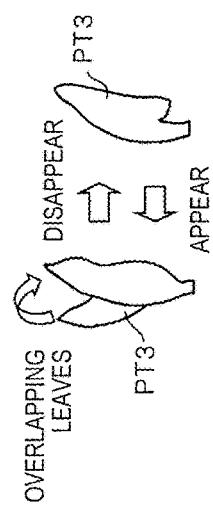
FIG. 21B is a diagram illustrating overlapping of leaves.

In addition, the leaves of a seedling in a field grow in abundance and become foliage. In the foliage, a plurality of leaves overlap is respective orientations, and for example, when wind blows, the leaves relatively move. For example, as shown in FIG. 21A, in a case where the near infrared beam is radiated toward leaf PT3t that is the measurement target, the radiated near infrared beam is absorbed and scattered by leaf PT3o that is on the periphery of leaf PTt that is the measurement target. As indicated by arrow b1, other than, for example, the radiated near infrared beam being absorbed by leaf PT3t that is the measurement target, as indicated by arrow b2, leaf PT3o on the left side is also radiated and a portion is absorbed. Leaf PT3o on the left side is radiated, and the near infrared beam that is scattered by leaf PT3o on the left side is diffused on leaf PT3t that is the measurement target. In addition, as indicated by arrow b3, multiple scattering also occurs in which leaf PT3$r$1 on the right side is radiated, and diffused light that is scattered by leaf PT3$r$1 on the right side is diffused to other leaf PT3$r$2 and is diffused on leaf PT3$t$ that is the measurement target. Water content of target leaf PT3$t$ contains the water content absorbed by the peripheral leaf, and is measured to be greater than in reality. In addition, as shown in FIG. 21B, a plurality of leaves overlap or are separated, and the area of the leaf is changed.

Accordingly, even in measurement of presence or absence of water content, individual leaves on the periphery of the target leaf are difficult to distinguish.

Therefore, it is possible to eliminate influence due to scattered light (for example, light scattered externally such as sunlight) from the peripheral leaf and accurately measure water content of the leaf that is the measurement target even within the foliage in which multiple leaves grow in abundance.

Second Embodiment

A configuration of a water content evaluation apparatus of the second embodiment is substantially the same configuration as the first embodiment. The same reference numerals are used for the configuring elements which are the same as in the first embodiment, and therefore the description is omitted.

The leaf of the plant that is the measurement target is a leaf that is representative of the plant in for example, a plastic greenhouse, temperature, humidity, illumination, and ventilation are set in a location with different $CO_2$ concentrations.

FIG. 21A is a diagram which describes a summary of an operation of the water content evaluation apparatus in the second embodiment. FIG. 21B is a diagram illustrating overlapping of leaves. In the water content evaluation apparatus, a background material is disposed so as to cover a back surface (rear side) of the leaf that is the measurement target.

As the material of the background material, a material that does not contain water and that does not deform due to pesticide, sprinkling, or $CO_2$ spraying is given such as plastic, coated paper, sheets such as aluminum foil (plate), a plate, or a block. In addition, it is desirable that the size of the background material has a large surface such that the leaf that is the measurement target is covered and is a size so as not to interfere with photosynthesis of another leaf within two times the projection area of the leaf that is the measurement target. In addition, it is preferable that the thickness of the background material is a thickness of 50 μm to 1 mm self-supporting without curling, and in particular, 50 to 200 μm. In addition, in a case of being supported by the stalk of the leaf, it is preferable that the weight of the background material is a weight to a degree that the leaf does not wilt. In addition, it is preferable that the color of the background material is white or silver with high reflectance of visible light and the near infrared beam.

In the present embodiment, as the background material, a case of using a white reference substrate is indicated. Note that, a white plastic plate, an aluminum plate, a standard white plate, white paper, and the like are given as the white reference substrate.

FIG. 22A is a graph illustrating reflection light intensity with respect to wavelength of the near infrared beam when near infrared beam is radiated toward the leaf outdoors. The vertical axis indicates intensity of the near infrared light which is detected by invisible light sensor NVSS, and the horizontal axis indicates wavelength of a near infrared area. Intensity of light that is scattered by the peripheral leaf other than intensity of light according to sunlight is included in intensity of the near infrared light which is detected by invisible light sensor NVSS. That is, a rise of the background due to multiple scattering of sunlight being carried out on the peripheral leaf is included in the intensity of the detected near infrared light. In addition, intensity of light detected by invisible light sensor NVSS is small due to the near infrared beam which has a wavelength of 1550 nm being absorbed by the peripheral leaf. Accordingly, the value of reflection intensity rate Ln (I905/I1550) is large. Therefore, in a case where water content of the leaf outside is measured, it is necessary to set the value of threshold level Sh that is compared to reflection intensity rate Ln (I905/I1550) to be large.

Figure 22B:
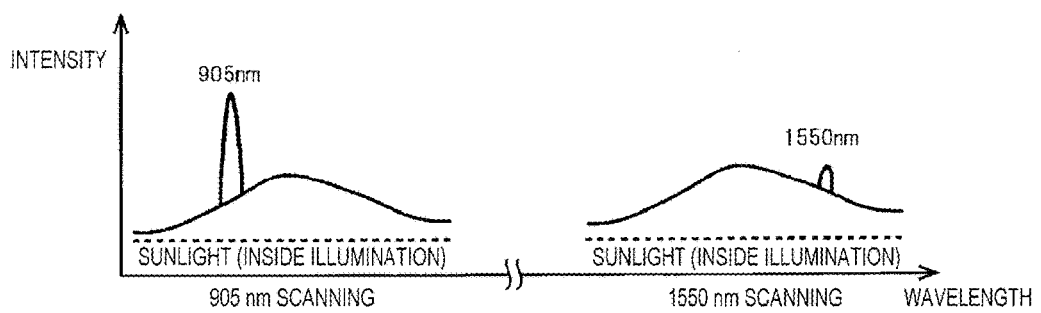
FIG. 22B is a graph illustrating a reflection light intensity with respect to a wavelength of the near infrared beam when the near infrared beam is radiated toward the leaf on which a white reference substrate is installed indoors and outdoors.

FIG. 22B is a graph illustrating reflection light intensity with respect to wavelength of the near infrared beam when near infrared beam is radiated toward the leaf on which white reference substrate bd is installed indoors and outdoors. The vertical axis indicates intensity of the near infrared beam which is detected by invisible light sensor NVSS, and the horizontal axis indicates the wavelength of a near infrared area. Multiple scattering from peripheral leaf PT3$o$ does not occur due to white reference substrate bd being disposed to cover the back surface (rear side) of leaf PT3$t$ that is the measurement target. Accordingly, a lowering of intensity of the near infrared beam which has a wavelength of 1550 nm does not occur. In addition, in the case of inside, a rise of the background does not occur. Note that, in a case of measuring outside, threshold level Sh is set to approximately 0.5. In addition, in a case of measuring inside, threshold level Sh is set to approximately 0.3.

In a case where white reference substrate bd is disposed on the back surface of leaf PT3$t$ that is the measurement target, the leaf may be disposed without being fixed, and leaf PT3$t$ may be attachably fixed to white reference substrate bd. Here, a case where leaf PT3$t$ is attached to white reference substrate bd is illustrated.

FIG. 23 is a diagram which describes attachment of leaf PT3$t$ on white reference substrate bd. White reference substrate bd is a white plastic plate which has a vertical rectangular shape. Aperture bd1 that is hollowed out in a rectangular shape is formed in the center of white reference substrate bd. In addition, round hole bd2 is formed in an upper portion of white reference substrate bd. Slit bd21 which reaches up to an upper end surface is formed on hole bd2. In addition, three slits bd3, bd4, and bd5 are respectively formed on the lower side and both sides of aperture bd1 that is formed on white reference substrate bd.

In a case where leaf PT3$t$ is attached to white reference substrate bd, a tip end of leaf PT3$t$ is inserted into one of three slits bd3, a void is generated by shifting horizontal white reference substrate bd in a longitudinal direction centered on slit bd21, stalk PT2 of the leaf passes inside, and stalk PT2 is fixed to hole bd2.

Figure 24:
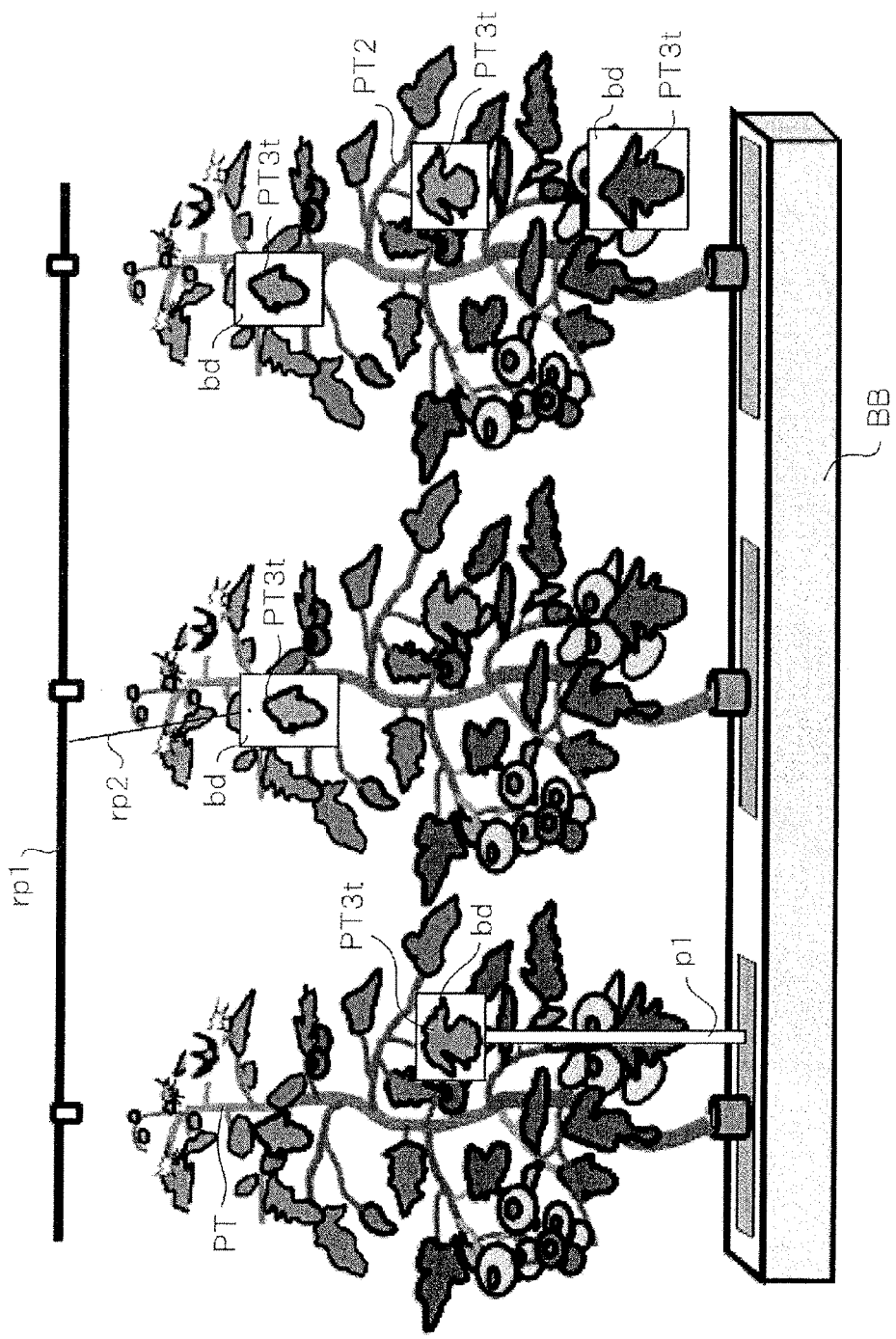
FIG. 24 is a diagram illustrating various installation methods of the white reference substrate that is installed so as to cover the back surface of the leaf that is a measurement target.

FIG. 24 is a diagram illustrating various installation methods of white reference substrate bd that is installed so as to cover the rear surface of leaf PT3$t$ that is a measurement target. In the diagram, in plant PT on the left side, white reference substrate bd is attached to the tip end of rod p1 that stands on base BB, and is installed as a notice board. In addition, in center plant PT, white reference substrate bd is held in a state of hanging down from attractant line rp1 due to attractant string rp2. In addition, in plant PT on the right side in the diagram, white reference substrate bd is held by stalk PT2 that passes through round hole bd2.

Figure 25A:
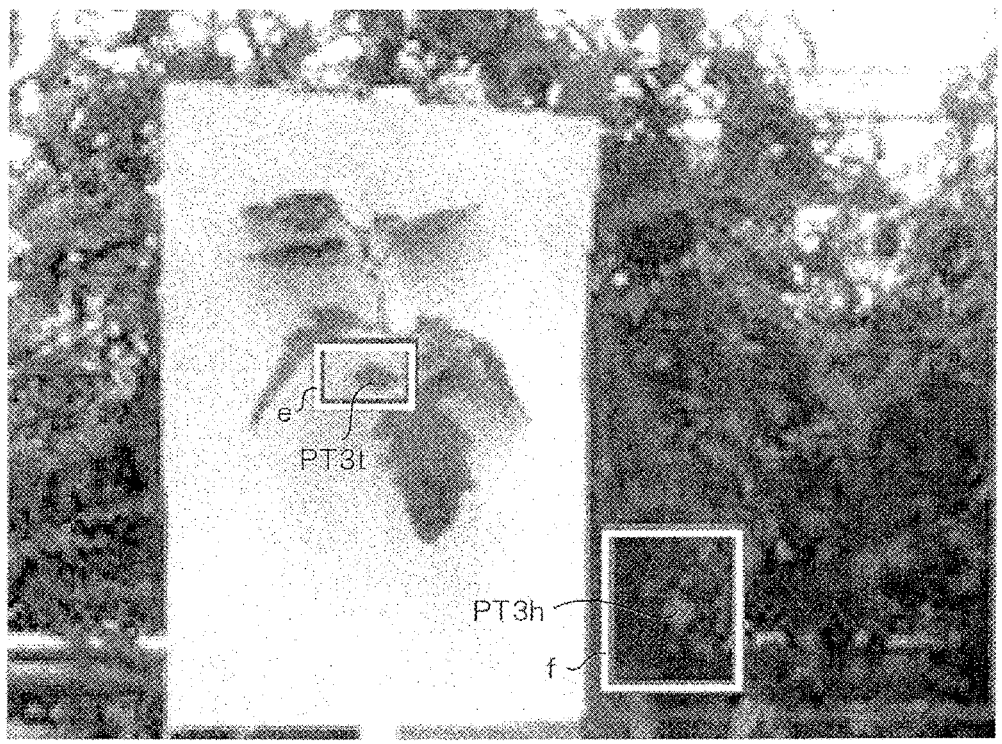
FIG. 25A is a photo illustrating the leaf that is the measurement target of water content outside.

FIG. 25A is a photo illustrating leaf PT3t that is the measurement target of water content outside. Here, white reference substrate bd is installed as the notice board. In addition, plurality of leaves PT3 protrude to stalk PT2 which protrudes from hole bd2 of white reference substrate bd, and one leaf (leaf enclosed by frame e) PT3t therein is set as the measurement target. In addition, as a comparative example, leaf (leaf enclosed by frame f in the diagram) PT3h on which the white reference substrate is not disposed on the back surface is set as the measurement target.

Figure 25B:
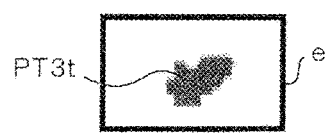
FIG. 25B is a diagram illustrating reflection intensity rate Ln (I905/I1550) of the leaf.
Figure 25C:
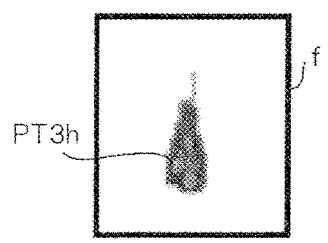
FIG. 25C is a diagram illustrating reflection intensity rate Ln (I905/I1550) of the leaf.

FIG. 25B is a diagram illustrating reflection intensity rate Ln (I905/I1550) of leaf PT3t. FIG. 25C is a diagram illustrating reflection intensity rate Ln (I905/I1550) of leaf PT3h. On leaf PT3h, since white reference substrate bd is not present, reflection intensity rate of leaf PT3h is increased due to scattered light of the leaf in the periphery due to sunlight.

Figures 26A, 26B:
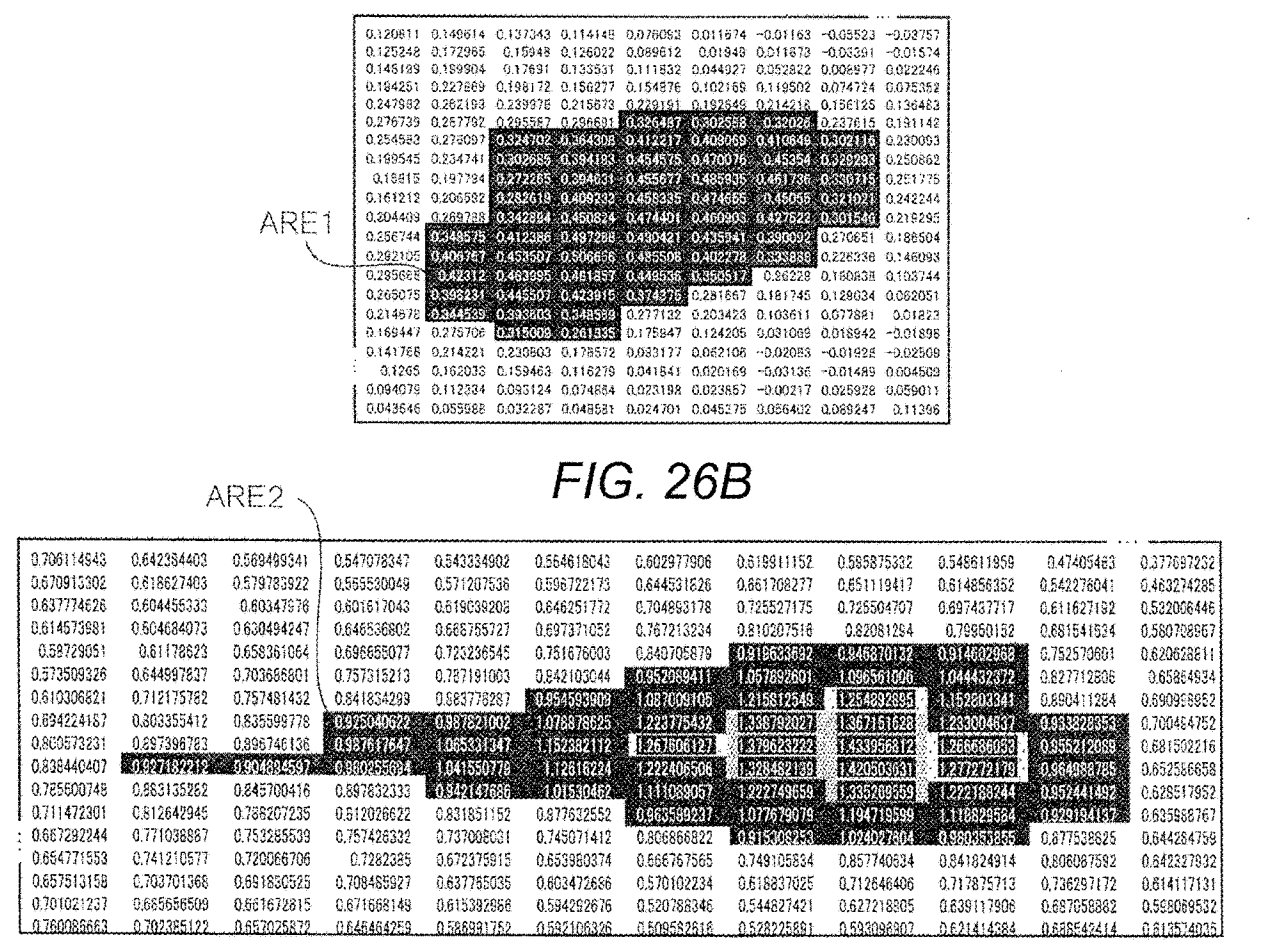

FIG. 26A is a table illustrating the reflection intensity rate in a portion of a frame image which includes a pixel space that leaf PT3t occupies which is covered by the back surface on white reference substrate bd. Area ARE1 in which reflection intensity rate Ln (I905/I1550) of leaf PT3t exceeds threshold level Sh (=0.3) is close to the shape of leaf PT3t, and it is considered that the outer form of the leaf is expressed. Meanwhile, FIG. 26B is a table illustrating the reflection intensity rate in a portion of the frame image which includes the pixel space that leaf PT3h occupies which is not covered by the back surface on white reference substrate bd. Reflection intensity rate Ln (I905/I1550) of leaf PT3h is large due to scattered light from peripheral leaf PT3o, and it is considered that an error is included. In addition, area ARE2 in which reflection intensity rate Ln (I905/I1550) of leaf PT3h exceeds threshold level Sh (=0.9) is not similar to the outer form of leaf PT3h that is slightly vertically shaped, and it is considered that the outer form of leaf PT3h is not expressed.

Figure 27:
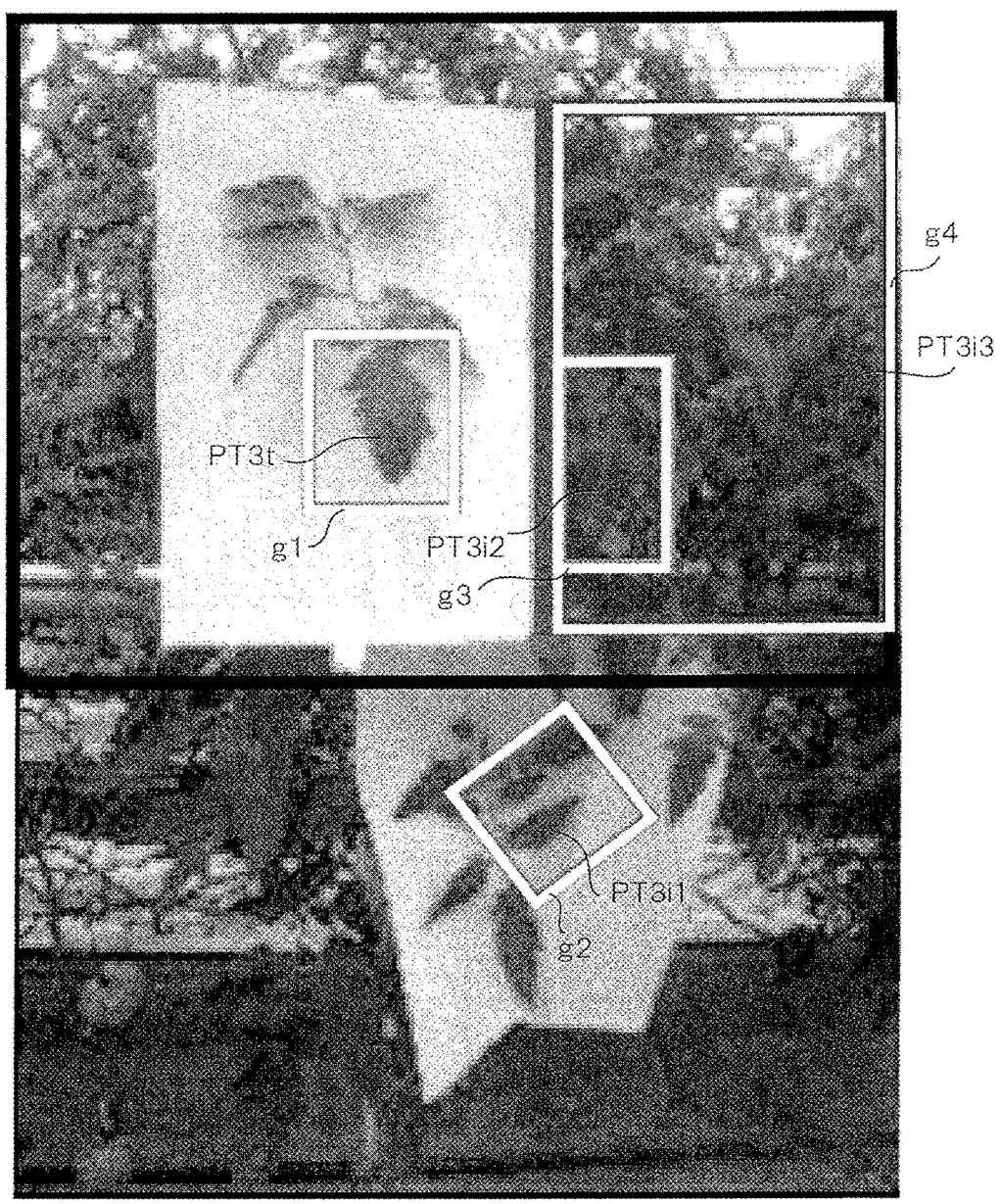
FIG. 27 is a photo illustrating the leaf that is the measurement target of half of the water content outside.

FIG. 27 is a photo illustrating the leaf that is the measurement target of half of the water content outside. In a first half measurement, leaf PT3t that is a high location is set as the measurement target enclosed by frame g1, and white reference substrate bd is disposed on the back side. In a second half measurement, leaf PT3i1 that is a low location is set as the measurement target enclosed by frame g2, and white reference substrate bd is disposed on the back side. In a third half measurement, plurality of leaves PT3i2 are set as measurement targets enclosed by frame g3, and nothing is disposed on the back side. In a fourth half measurement, foliage PT3i3 in which multiple leaves grow in abundance is set as the measurement target enclosed by large frame g4, and nothing is disposed on the back side.

Figure 28A:
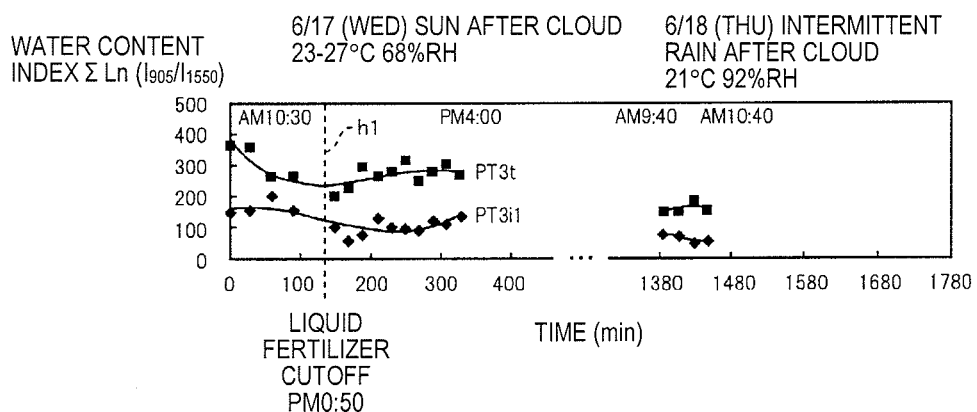
FIG. 28A is a graph illustrating the time change of the water content index of the leaf in a first half measurement and the leaf in a second half measurement.

FIG. 28A is a graph illustrating the time change of the water content index of leaf PT3t in the first half measurement and leaf PT3i1 in the second half measurement. The vertical axis is the water content index which is expressed by reflection intensity rate Ln (I905/I1550), and the horizontal axis is time (unit: mins). In addition, presence or absence of a half is determined according to whether or not the water content index is halved to ½ from a liquid fertilizer that is supplied to the plant being cut off (refer to broken line hi). The same also applies to FIGS. 28B and 28C.

When white reference substrate bd is disposed on the back side, either leaf PT3t at the high location and leaf PT3i1 at the low location, and approximately 1200 minutes elapse from supply of the liquid fertilizer being cut off, half of the water content index is confirmed.

Figure 28B:
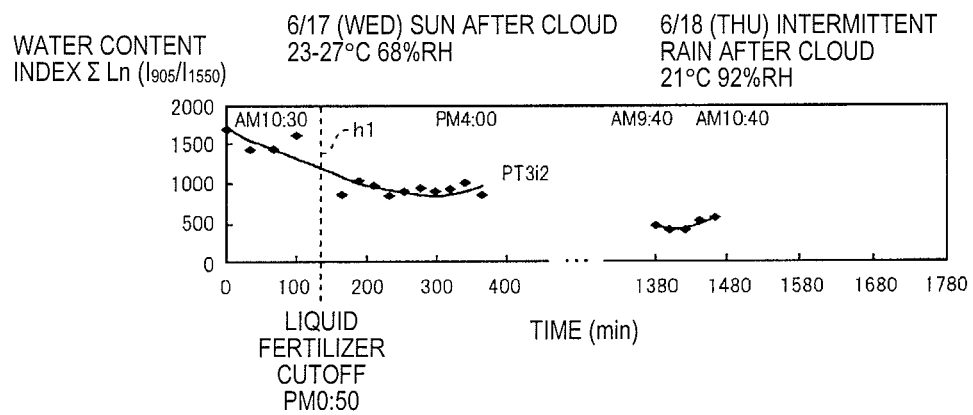
FIG. 28B is a graph illustrating the time change of the water content index of the leaf in a third half measurement.

FIG. 28B is a graph illustrating the time change of the water content index of leaf PT3i2 in the third half measurement. In leaf PT3i2 in which white reference substrate bd is not disposed on the back, although a background of reflection intensity rate Ln (I905/I1550) due to diffused reflection from the peripheral leaf is slightly large in comparison to leaf PT3t and PT3i1, when approximately 1200 minutes elapse from supply of the liquid fertilizer being cut off, half of the water content index is confirmed.

Figure 28C:
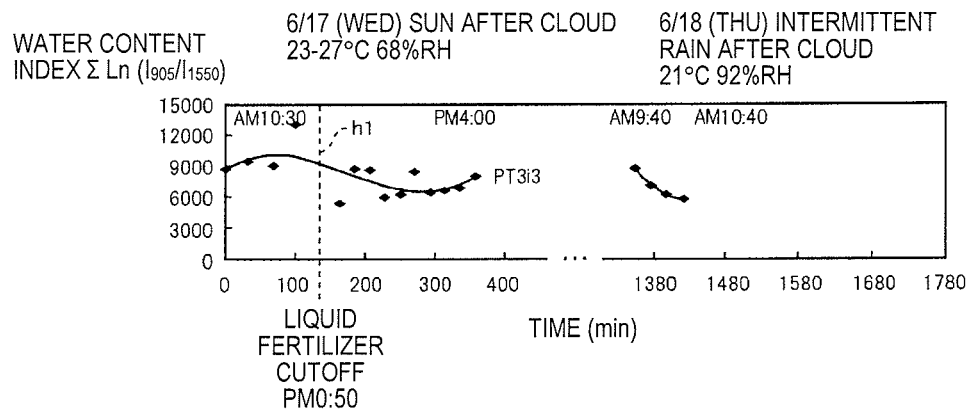
FIG. 28C is a graph illustrating the time change of the water content index of foliage in a fourth half measurement.

FIG. 28C is a graph illustrating the time change of the water content index of foliage PT3i3 in the fourth half measurement. In leaf PT3i3 in which white reference substrate bd is not disposed on the back surface, although the background of reflection intensity rate Ln (I905/I1550) due to diffused reflection (light scattered externally) from the peripheral leaf is significantly large, when approximately 1200 minutes elapse from supply of the liquid fertilizer being cut off, half of the water content index is not able to be confirmed. Accordingly, in the foliage, even if overlapping leaves (refer to FIG. 21B) appear or disappear, and reflection intensity rate Ln (I905/I1550) is measured, it is understood that the error is large.

In this manner, in the water content evaluation apparatus in the second embodiment, when the water content of the leaf (or the part of the plant) is evaluated, white reference substrate bd (background material) is disposed so as to cover the back surface of leaf PT3 of plant PT. First beam source 13 radiates near infrared beam (reference beam) of wavelength 905 nm that has a characteristic of tending not to be absorbed in water toward leaf PT3 by optical scanning. Second beam source 15 radiates near infrared beam (measuring beam) of wavelength 1550 nm that has a characteristic of tending to be absorbed in water toward leaf PT3 by optical scanning. Threshold level setter/water content index detector 27a calculates the water content index of one leaf that is total sum Σ Ln (I905/I1550) of the reflection intensity rate at all irradiation positions of leaf PT3 based on the reflection light of the reference beam that is reflected on all irradiation positions of leaf PT3 and the reflection light of the measuring beam that is reflected on all irradiation positions of leaf. PT3. Thereby, it is possible to eliminate influence due to scattered light (light scattered externally) from the peripheral leaf and accurately measure the water content of the leaf that is the measurement target by removing influence of overlap and the like even within the foliage in which multiple leaves grow in abundance.

In addition, white reference substrate bd is the notice board standing in front of leaf PT3 of the plant. Thereby, it is possible to dispose white reference substrate bd in a state of being installed independently from the plant, and it is possible to firmly fix. Accordingly, even to the extent of external force or disbudding of wind, rain, and the like, and artificial external force during leaf work being applied, it is possible to maintain a posture of white reference substrate bd.

In addition, white reference substrate bd hangs down from above the plant using attractant string rp2. Thereby, it is possible to dispose white reference substrate bd in a state in which leaf PT3 of the plant is separated, or it is possible to follow to an extent at which attachment to white reference substrate bd is growth of the stalk with ease (growth rate of tomato seedling is approximately 1 cm/day).

In addition, white reference substrate bd is supported on stalk PT2 of the plant. Thereby, it is possible to easily dispose white reference substrate bd on a reverse side of the leaf without using another support member, and it is possible to follow to an extent of growth of the stalk (growth rate of tomato seedling is approximately 1 cm/day).

Although various embodiments are described above while referring to the drawings, needless to say, the present disclosure is not limited to the examples. According to a person skilled in the art, within the scope which is set forth in the claims, it is obvious that it is possible to conceive of various modified examples and correction examples, and therein is naturally understood as belonging to the technical scope of the present disclosure.

The present disclosure is able to set various products in which a drying process is provided in a manufacturing process as the measurement target other than the leaf of the plant that is set as the measurement target.

For example, as one product in which the drying process is provided in the manufacturing process, a flexible substrate and the like is considered. When the flexible substrate is produced, in a heat drying process, a reaction rate of a polyimide of a coating member, that is, an imidization rate is important. The imidization rate is obtained by measuring the water content of the coating member, and calculating the water content that is evaporated from the coating member. It is possible to improve quality of the flexible substrate if the water content evaluation apparatus of the present disclosure is applied to the heat drying process of the flexible substrate.

In addition, as the product in which the drying process is provided in the manufacturing process, ceramics, a wall of a building, nori seaweed, wakame seaweed, dry matter such as dried squid, a confection, paper, and the like are given. In the respective drying process, if applied to take advantage of the water content evaluation apparatus of the present disclosure, the water content of the product is as small as possible, or an adequate water content, however it is possible to measure whether or not there is a state in which unevenness is slight, and it is possible to improve quality of the product.

What is claimed is:

1. A water content evaluation apparatus which evaluates water content of a part of a plant, the water content evaluation apparatus comprising:
    a first light source which radiates a laser reference beam of a first wavelength toward a plant at irradiation positions of the plant, the laser reference beam of the first wavelength not being absorbed by water;
    a second light source which radiates a laser measuring beam of a second wavelength toward the plant at the irradiation positions of the plant, the laser measuring beam of the second wavelength being absorbed by water; and
    a controller that executes instructions, the instructions, when executed by the controller, causing the controller to perform operations including:
        calculating water content of the plant at each of the irradiation positions of the plant based on a first reflection light of the laser reference beam that is reflected at all the irradiation positions of the plant and a second reflection light of the laser measuring beam that is reflected at all the irradiation positions of the plant, and
        calculating the water content at all the irradiation positions of the plant by adding the water content calculated at each of the irradiation positions.

2. The water content evaluation apparatus of claim 1, wherein the operations further include:
    holding a threshold level which indicates the water content and identifies a shape of the plant; and
    adding water at at least one of the irradiation positions when the one of the irradiation positions is at the threshold level or more.

3. The water content evaluation apparatus of claim 2, wherein the operations further including:
    acquiring a visible light image of the plant; and
    calculating the threshold level using the visible light image of the plant.

4. The water content evaluation apparatus of claim 1, wherein the operations further include:
    outputting at least one invisible light image of a leaf, a seed, a stalk, and a flower of the plant.

5. The water content evaluation apparatus of claim 4, wherein the operations further include:
    displaying the invisible light image with the water content which is calculated at each of the irradiation positions being identifiable.

6. The water content evaluation apparatus of claim 4, wherein each of the irradiations position corresponds to a pixel of a predetermined number in the invisible light image.

7. The water content evaluation apparatus of claim 1, wherein the first light source radiates a near infrared laser reference beam as the laser reference beam, and
    the second light source radiates a near infrared laser measuring beam as the laser measuring beam.

8. The water content evaluation apparatus of claim 1, wherein the controller is a processor.

9. A water content evaluation apparatus, comprising:
    a first light source which radiates a laser reference beam of a first wavelength toward irradiation positions which are included in a part of a plant that is set as an evaluation target, a background material covering a back surface of the part of the plant, the laser reference beam of the first wavelength not being absorbed by water;
    a second light source which radiates a laser measuring beam of a second wavelength toward the irradiation positions, the laser measuring beam of the second wavelength being absorbed by water;
    a controller that executes instructions, the instructions, when executed by the controller, causing the controller to perform operations including:
        identifying the part of the plant that is the evaluation target based on a first reflection light of the laser reference beam that is reflected at the irradiation positions of the part of the plant and a second reflection light of the laser measuring beam that is reflected at the irradiation positions of the part of the plant;
        calculating water content of the part of the plant that is the evaluation target at each of the irradiation positions of the plant based on the first reflection light of the laser reference beam that is reflected at all the irradiation positions of the part of the plant and the second reflection light of the laser measuring beam that is reflected at all the irradiation positions of the part of the plant; and
        calculating the water content of the part of the plant that is the evaluation target at all the irradiation positions of the part of the plant by adding the water content calculated at each of the irradiation positions.

10. The water content evaluation apparatus of claim 9, wherein the first light source radiates a near infrared laser reference beam as the laser reference beam, and
    the second light source radiates a near infrared laser measuring beam as the laser measuring beam.

11. The water content evaluation apparatus of claim 9, wherein the controller is a processor.

12. A water content evaluation method for a water content evaluation apparatus, the water content evaluation method comprising:

causing a first light source to radiate a laser reference beam of a first wavelength toward a plant at irradiation positions of the plant, the laser reference beam of the first wavelength not being absorbed by water;

causing a second light source to radiate a laser measuring beam of a second wavelength toward the plant at the irradiation positions of the plant, the laser measuring beam of the second wavelength being absorbed by water;

calculating, by a controller, water content of the plant at each of the irradiation positions of the plant based on a first reflection light of the laser reference beam that is reflected at all the irradiation positions of the plant and a second reflection light of the laser measuring beam that is reflected at all the irradiation positions of the plant; and calculating, by the controller, the water content at all the irradiation positions of the plant by adding the water content calculated at each of the irradiation positions.

13. The water content evaluation method of claim 12, wherein the first light source radiates a near infrared laser reference beam as the laser reference beam, and the second light source radiates a near infrared laser measuring beam as the laser measuring beam.

14. The water content evaluation method of claim 12, wherein the first light source radiates a near infrared laser reference beam as the laser reference beam, and the second light source radiates a near infrared laser measuring beam as the laser measuring beam.

15. A water content evaluation method for a water content evaluation apparatus, the water content evaluation apparatus evaluating water content of a part of a plant, the water content evaluation method comprising:

covering a back surface of the part of the plant with a background material, the part of the plant being set as an evaluation target of the water content evaluation apparatus;

causing a first light source to radiate a laser reference beam of a first wavelength toward irradiation positions which comprise the part of the plant that is set as the evaluation target and the background material, the laser reference beam of the first wavelength not being absorbed by water;

causing a second light source to radiate a laser measuring beam of a second wavelength toward the irradiation positions, the laser measuring beam of the second wavelength being absorbed by water;

identifying, by a controller, the part of the plant that is set as the evaluation target based on a first reflection light of the laser reference beam that is reflected at the irradiation positions of the part of the plant and a second reflection light of the laser measuring beam that is reflected at the irradiation positions of the part of the plant;

calculating water content of the part of the plant that is set as the evaluation target at each of the irradiation positions of the plant based on the first reflection light of the laser reference beam that is reflected at all the irradiation positions of the part of the plant and the second reflection light of the laser measuring beam that is reflected at all the irradiation positions of the part of the plant; and calculating the water content of the part of the plant that is the evaluation target at all the irradiation positions of the part of the plant by adding the water content calculated at each of the irradiation positions.

16. The water content evaluation method of claim 15, wherein a reflection intensity rate is calculated at each of the irradiation positions that is irradiated with the laser reference beam and the laser measuring beam based on a first rate of a first reflection intensity of the laser reference beam and a second rate of a second reflection intensity of the laser measuring beam, and the irradiation positions at which the calculated reflection intensity rate exceeds a threshold level are set as the part of the plant that is the evaluation target.

17. The water content evaluation method of claim 16, wherein the threshold level, corresponding to a cumulative frequency of the reflection intensity rate, is obtained so as to be a same pixel number as an occupied pixel number of a specific color of the part of the plant that is the evaluation target in a visible light image of the irradiation area, the visible light image being imaged by a visible light camera.

18. The water content evaluation method of claim 16, wherein an irradiation position at which the calculated reflection intensity rate is the threshold level or less is set as outside the evaluation target of the water content evaluation apparatus.

19. The water content evaluation method of claim 15, wherein the part of the plant that is set as the evaluation target is at least one of a leaf, a seed, a stalk, and a flower of the plant.

* * * * *